(12) United States Patent
Kim et al.

(10) Patent No.: US 8,772,021 B2
(45) Date of Patent: Jul. 8, 2014

(54) EXPRESSION VECTOR FOR ANIMAL CELL COMPRISING AT LEAST ONE COPY OF MAR DNA SEQUENCES AT THE 3' TERMINAL OF TRANSCRIPTION TERMINATION REGION OF A GENE AND METHOD FOR THE EXPRESSION OF FOREIGN GENE USING THE VECTOR

(75) Inventors: Jong-mook Kim, Incheon (KR); Hye-jin Hong, Incheon (KR); Hyun-joo Lee, Incheon (KR); Moon-kyoung So, Bucheon (KR); Soo-young Lee, Incheon (KR); Jong-moon Cho, Incheon (KR); Bok-hwan Chun, Suwon (KR); Seung-suh Hong, Daejeon (KR); Myung-sam Cho, Incheon (KR)

(73) Assignee: Celltrion, Inc. (KR)

( * ) Notice: Subject to any disclaimer, the term of this patent is extended or adjusted under 35 U.S.C. 154(b) by 1680 days.

(21) Appl. No.: 11/817,756

(22) PCT Filed: Mar. 4, 2006

(86) PCT No.: PCT/KR2006/000753
§ 371 (c)(1),
(2), (4) Date: Sep. 4, 2007

(87) PCT Pub. No.: WO2006/093397
PCT Pub. Date: Sep. 8, 2006

(65) Prior Publication Data
US 2008/0102523 A1    May 1, 2008

(30) Foreign Application Priority Data
Mar. 4, 2005   (KR) ................. 10-2005-0018130

(51) Int. Cl.
*C12N 15/00*   (2006.01)
(52) U.S. Cl.
USPC ..................................... 435/320.1; 435/455
(58) Field of Classification Search
None
See application file for complete search history.

(56) References Cited

U.S. PATENT DOCUMENTS

| | | |
|---|---|---|
| 6,177,612 B1 | 1/2001 | Jordan et al. |
| 6,245,974 B1 | 6/2001 | Michalowski et al. |
| 6,388,066 B1 | 5/2002 | Bruce et al. |
| 2004/0072352 A1 | 4/2004 | Kim et al. |
| 2004/0115776 A1 | 6/2004 | Simesen et al. |

FOREIGN PATENT DOCUMENTS

| | | |
|---|---|---|
| KR | 1020020010327 A | 2/2002 |
| WO | 0021425 | 4/2000 |
| WO | 0214525 A2 | 2/2002 |
| WO | 0248379 A1 | 6/2002 |
| WO | 03024199 A2 | 3/2003 |

OTHER PUBLICATIONS

Kurre, P., et al.; "Scaffold attachment region-containing retrovirus vectors improve long-term proviral expression after transplantation of GFP-modified CD34+ baboon repopulating cells;" Blood; vol. 102; pp. 3117-3119; 2003.
Yu, J., et al.; "A 5' beta-globin matrix-attachment region and the polyoma enhancer together confer position-independent trascription;" Gene; vol. 139; pp. 139-145; 1994.
Namciu, S.J., et al.; "Human matrix Attachment Regions Are Necessary for the Establishment but Not the Maintenance of Transgene Insulation in *Drosophila melanogaster*;" Molecular and Cellular Biology; vol. 24, No. 23; pp. 10236-10245; Dec. 2004.
Genbank Accession No. L22754, Oct. 11, 2005.
Pienta, K. J., et al.; "Cell Structure and DNA Organization"; Critical Reviews in Eukaryotic Gene Expression; vol. 1, Issue 4; pp. 355-385; 1991.
European Search Report dated Aug. 20, 2008 for Application No. 06716203.2-2405.

*Primary Examiner* — Catherine Hibbert
(74) *Attorney, Agent, or Firm* — Cantor Colburn LLP

(57) ABSTRACT

Provided are an expression vector for an animal cell including a promoter, a cloning site or a polynucleotide encoding foreign product, and a transcription terminator, all of which are operably connected each other within the expression vector, in which at least one copy of human β-globin MAR sequence is attached to the 31 terminal of the transcription terminator, and a method of expressing a foreign gene using the expression vector.

7 Claims, 12 Drawing Sheets

_US 8,772,021 B2_

EXPRESSION VECTOR FOR ANIMAL CELL COMPRISING AT LEAST ONE COPY OF MAR DNA SEQUENCES AT THE 3' TERMINAL OF TRANSCRIPTION TERMINATION REGION OF A GENE AND METHOD FOR THE EXPRESSION OF FOREIGN GENE USING THE VECTOR

TECHNICAL FIELD

The present invention relates to an expression vector for an animal cell comprising a nuclear matrix attachment region (MAR) element, and a method of expressing a gene using the same.

BACKGROUND ART

Extensive research has been conducted into the role of matrix attachment region (MAR) DNA sequences in the regulation of eukaryotic gene expressions. A MAR sequence (also referred to as a scaffold attachment region (SAR)) is an exemplary element used in the regulation of transcription. In general, a MAR sequence is known to be effective only when inserted into a host genome. It is also known that a MAR sequence, particularly one that is highly rich in AT to an extent of about 70% or greater, increases a transgene expression in an animal cell line that has been stably transformed. It is also known that when a MAR sequence is used, the expression variability of various transformants is low. Such a position-independent expression is believed to be due to the MAR sequence which protects inserted DNA from the intervening effect of neighboring chromatin enhancer or silencer, or inhibits methylation of the inserted DNA, thus insulating foreign DNA inserts from the position effect.

MAR sequences are frequently used to increase expression of foreign genes in animal cells. For example, WO 02/1425 discloses an expression vector containing β-globin MAR sequence at the 5' terminal of the promoter. U.S. Pat. No. 6,388,066 also discloses a promoter-driven structure containing corn ADH1 MAR DNA sequence which is located adjacent to a combined element consisting of a promoter, a nucleotide sequence operably connected to the promoter, and a transcription termination region. However, a DNA structure having two or more MAR DNA sequences sequentially introduced at the 3' terminal of a transcription terminator has not been introduced so far.

Even though the technologies as described above are available in the related art, there is still a demand for an expression vector that is capable of expressing foreign genes in animal cells with higher efficiency. While investigating a method of increasing foreign gene expression, the inventors of the present invention have found that foreign gene expression is markedly increased when at least one copy of a MAR DNA sequence is introduced at the 3' terminal of a transcription terminator of a gene and completed the present invention.

DETAILED DESCRIPTION OF THE INVENTION

Technical Problem

Figure 1:
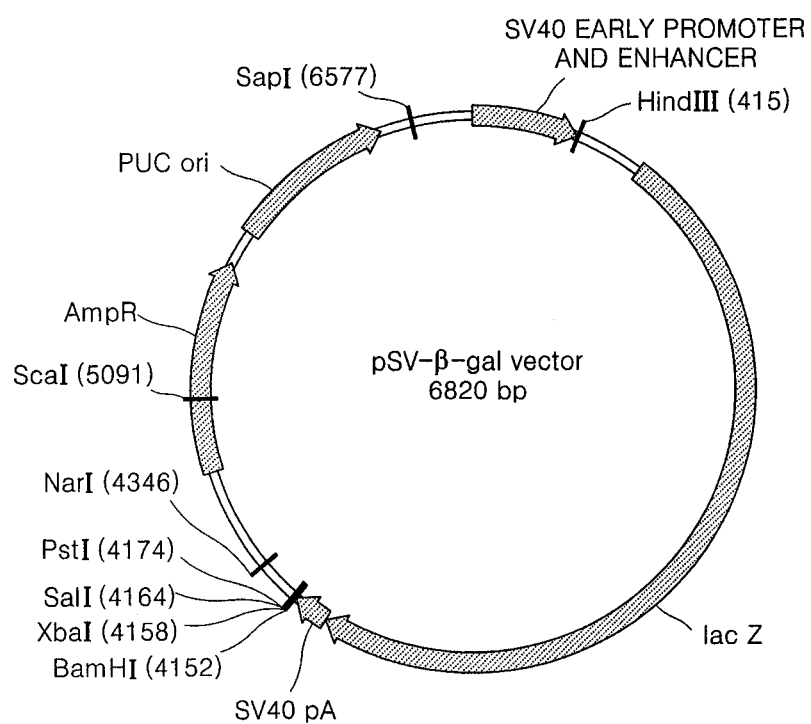
FIG. 1 is a diagram illustrating a commercially available pSV-β-gal vector (Promega Corp., US), which contains a SV40 early promoter and a lacZ gene operably connected thereto.

The present invention provides an expression vector for an animal cell that is capable of efficiently expressing a foreign gene.

The present invention also provides a method of efficiently expressing a foreign gene using the expression vector for the animal cell.

Technical Solution

According to an aspect of the present invention, there is provided an expression vector for an animal cell containing a promoter, a cloning site or a polynucleotide encoding foreign product, and a transcription terminator, all of which are operably connected to the expression vector, in which at least one copy of human β-globin MAR sequence is attached to the 3' terminal of the transcription terminator.

The promoter according to an embodiment of the present invention may be any conventionally known promoter. Examples of the promoter include expression vectors such as SV40 early promoter (e.g., a polynucleotide containing nucleotides 1 to 419 of SEQ ID NO:1), and CMV-derived promoter (e.g., a polynucleotide containing nucleotides 1 to 684 of SEQ ID NO:6). The polynucleotide encoding foreign product according to an embodiment of the present invention may be any polynucleotide that can encode a foreign product such as a foreign protein or a foreign nucleic acid. The foreign product may be a protein such as lacZ, immunoglobulin, GCSF or EPO. The term "cloning site" refers to a nucleic acid sequence into which a restriction enzyme recognition site or cleavage site is introduced so as to allow foreign genes to be inserted into a vector.

According to an embodiment of the present invention, the transcription terminator may be any conventionally known transcription terminator. Examples of the transcription terminator include human growth hormone polyadenylation signal, bovine growth hormone polyadenylation signal, and SV40 virus polyadenylation signal. The transcription terminator according to an embodiment of the present invention may be SV40 virus polyadenylation signal (a polynucleotide comprising nucleotides 4021 to 4156 of SEQ ID NO:1).

According to an embodiment of the present invention, the term matrix attachment region (MAR) refers to a DNA sequence which transiently attaches a transcriptively active DNA loop domain to the filamentous protein network known as nuclear matrix (Pienta et al., *Crit. Rev. Eukaryotic Gene Express.*, 1:355-385 (1991)). Many examples of the MAR sequence are known in the related art, and one exemplary MAR sequence may be a sequence of Genbank accession number L22754 (a polynucleotide comprising nucleotides 4178 to 7142 of SEQ ID NO:1). According to an embodiment of the present invention, when two or more copies of MAR sequences are contained in the 3' terminal region of the transcription terminator, these two or more copies of MAR sequences may be connected adjacently to each other, or may be separated by a relatively short spacer region. For example, the two or more copies of MAR sequences may be connected sequentially and adjacently to each other. In addition, according to an embodiment of the present invention, the term "3' terminal of transcription terminator" refers to the 3' terminal of a transcription terminator, or in other words, a polyadenylation (polyA) signal. However, the 3' terminal of a polyadenylation signal is not necessarily intended to mean the exact 3' terminal of the polyadenylation signal only, and should be interpreted to encompass the downstream region of the 3' terminal that is under the influence of the polyadenylation signal.

Figure 14:
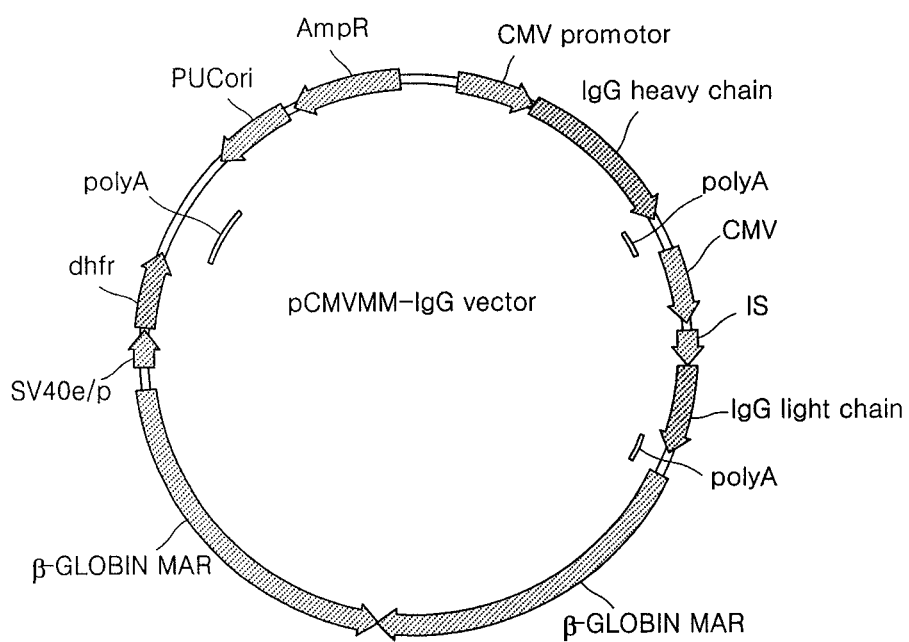
FIG. 14 is a diagram illustrating a pCMVMM-IgG vector, which has two copies of human β-globin MAR sequences sequentially attached to the 3' terminal of the transcription terminator (in the case of heavy chain, BGH polyA; in the case of light chain, SV40 polyA) of IgG gene of pCMV-IgG vector. The pCMVMM-IgG vector contains a dhfr gene as a selective gene.

An example of the expression vector according to an embodiment of the present invention is an expression vector having any one of the nucleotide sequences of SEQ ID NOs: 1, 2, 5, 6 and 7, or a pCMVMM-IgG expression vector having the vector map shown in FIG. 14. A vector having the sequence of SEQ ID NOs: 1, 2, 6 or 7 is such that the polynucleotide encoding foreign product is a gene encoding lacZ, while a vector having the sequence of SEQ ID NO:5 is such that the polynucleotide encoding foreign product is a gene encoding GCSF. The pCMVMM-IgG expression vector having the vector map shown in FIG. 14 is such that the polynucleotide encoding foreign product is a gene encoding an immunoglobulin heavy chain and light chain.

According to another aspect of the present invention, there is provided a method of expressing a foreign gene, comprising culturing an animal cell that is transfected with an expression vector according to an embodiment of the present invention.

In the method according to the present invention, the animal cell may be any animal cell, and examples thereof include cells selected from the group consisting of CHO, BHK, NS0 and human cells, but are not limited thereto. The animal cell may be a CHO cell. In addition, the method of culturing the animal cell may be any method that is known in the related art. A person having ordinary knowledge in the art would be able to appropriately select the culturing conditions such as medium, temperature, etc., in accordance with the selected cell line.

Advantageous Effects

The expression vector for an animal cell according to the present invention can be used to significantly increase expression of foreign genes in animal cells.

The gene expression method according to the present invention can be used to express genes in animal cells easily with high efficiency.

MODE OF THE INVENTION

Hereinafter, the present invention will be described in more detail with reference to examples. However, these examples are provided only for the purpose of illustrating the present invention and are not intended to limit the scope of the present invention.

EXAMPLES

The inventors of the present invention examined the effect of a MAR element that is contained in an expression vector for an animal cell and is attached to the 3' terminal of a transcription terminator of a gene, on the expression of the gene. To this end, first, a vector having one or two copies of human β-globin MAR sequences inserted at a downstream position of a SV40 polyadenylation signal was prepared. The prepared vector was introduced into animal cells, and the animal cells were cultured in order to observe the extent of expression of the gene.

Example 1

Preparation of Vector Containing MAR Sequence at the 3' Terminal of Gene

1. Isolation of Human β-globin 5' MAR.

First, HepG-2 cells were cultured, and genome DNA was isolated from the obtained HepG-2 cells using DNeasy Kit (Qiagen, US), according to the instruction provided by the manufacturer.

Subsequently, a polymerase chain reaction (PCR) was performed using the obtained genome DNA as a template, and using the oligonucleotides of SEQ ID NOs: 3 and 4 as primer, in order to amplify the 5' MAR sequence of human β-globin gene. PCR was performed under the conditions of 35 cycles of 15 minutes at 94° C., 1 minute at 94° C., 1 minute at 62° C. and 3 minutes at 72° C., and another cycle of 10 minutes at 72° C.

The PCR product thus obtained was inserted into a yT&A cloning vector (Yeastern Biotech Co., Ltd., Taiwan) to prepare a yT&A/β-globin MAR vector having the 5' MAR sequence of β-globin gene inserted therein. The yT&A cloning vector is a TA cloning vector designed to allow direct cloning of a PCR product without using a restriction enzyme.

2. Preparation of Expression Vector for Animal Cell Containing MAR Sequence at the 3' Terminal of Transcription Terminator of a Gene.

1) Preparation of pSVM-β-Gal and pSVMM-β-Gal Vectors, Both Having SV40 Early Promoter, lacZ Gene and SV40 Transcription Terminator Operably Connected Thereto and Having One Copy and Two Copies, Respectively, of Human β-Globin MAR Sequences Connected to the 3' Terminal of SV40 Transcription Terminator.

Using a pSV-β-gal vector (Promega, US) containing a SV40 early promoter and a lacZ gene operably connected to the promoter (See FIG. 1), an expression vector for an animal cell containing a MAR sequence at the 3' terminal of transcription terminator of a gene was prepared.

Figure 2:
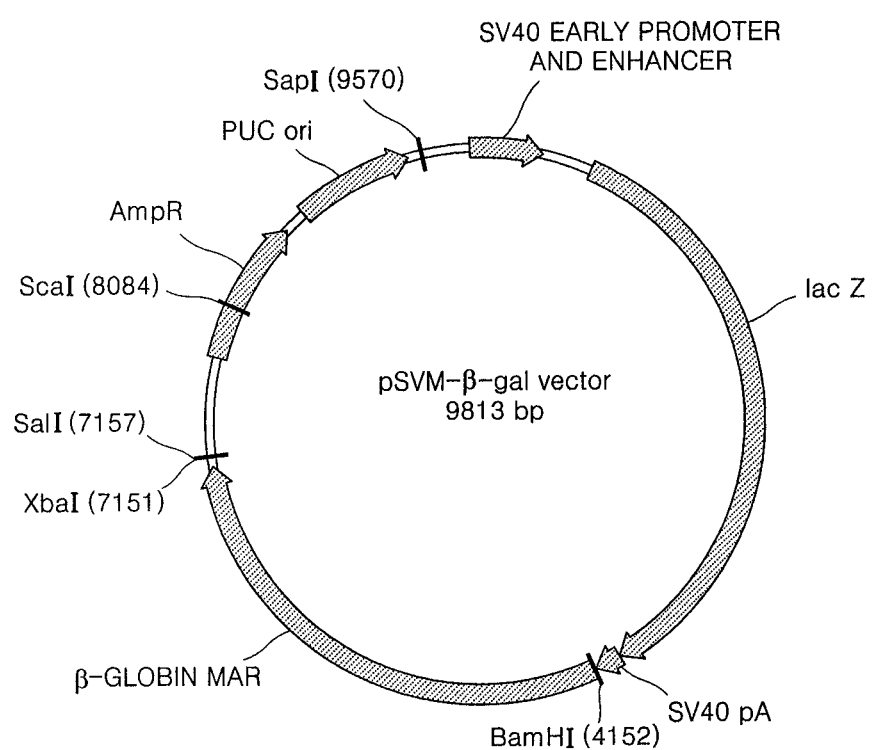
FIG. 2 is a diagram illustrating a pSVM-β-gal vector, which has one copy of human β-globin MAR sequence attached to the 3' terminal of a lacZ transcription termination region of a pSV-β-gal vector (Promega Corp.)

First, the yT&A/β-globin MAR vector obtained in Section 1 was treated with BamHI and XbaI, the product obtained from the treatment was isolated by agarose gel electrophoresis, and BamHI-XbaI product was isolated from the product obtained from the treatment. Next, the BamHI-XbaI product was ligated to a pSV-β-gal vector (Promega, US) that had been treated with BamHI and XbaI, and thus a pSVM-β-gal vector having one copy of human β-globin MAR sequence connected to the 3' terminal of the SV40 transcription terminator (See FIG. 2) was obtained. The nucleotide sequence of the pSVM-β-gal vector was the same as the sequence of SEQ ID NO: 1.

Figure 3:
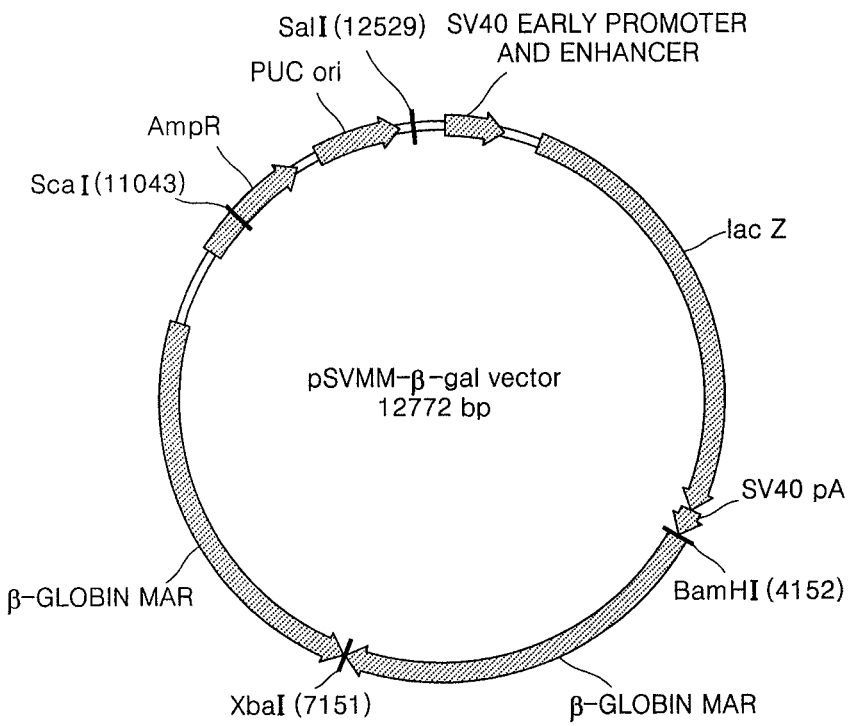
FIG. 3 is a diagram illustrating a pSVMM-β-gal vector, which has two copies of human β-globin MAR sequences attached to the 3' terminal of a lacZ transcription termination region of a pSV-β-gal vector (Promega Corp.)

Subsequently, the yT&A/β-globin MAR vector obtained in the above Section 1 was treated with XbaI and PstI, the product obtained from the treatment was isolated by agarose gel electrophoresis, and XbaI and PstI product was isolated from the product obtained from the treatment. Next, the XbaI-PstI product was ligated to a pSVM-β-gal vector that had been treated with XbaI and PstI, and thus a pSVMM-β-gal vector having two copies of human β-globin MAR sequences connected to the 3' terminal of the SV40 transcription terminator (See FIG. 3) was obtained. The nucleotide sequence of the pSVMM-β-gal vector was the same as the sequence of SEQ ID NO: 2.

2) Preparation of pCMVMM-β-Gal Vector Having CMV Promoter, lacZ Gene and SV40 Transcription Terminator Operably Connected Thereto, and Having Two Copies of Human β-Globin MAR Sequences Connected to the 3' Terminal of SV40 Transcription Terminator.

Using a pCMV-β-gal vector containing CMV promoter, lacZ gene and SV40 transcription terminator operably connected thereto, an expression vector for an animal cell containing two copies of human β-globin MAR sequence at the 3' terminal of transcription terminator of a gene was prepared.

First, in order to insert two copies of human β-globin MAR sequences into the pCMV-β-gal vector containing CMV early promoter, lacZ gene and transcription terminator, the pCMV-β-gal vector was treated with PmeI to open the vector, and then the opened pCMV-β-gal vector was isolated and purified using agarose gel electrophoresis. Subsequently, the opened pCMV-β-gal vector was treated with alkaline phosphatase to remove phosphate. After the removal of phosphate, the treatment product was heated at 65° C. for 15 minutes to deactivate the alkaline phosphatase, which was then removed by column chromatography. A pSVMM-β-gal vector was used to insert two copies of human β-globin MAR sequences into the opened pCMV-β-gal vector that had been treated as described above. The pSVMM-β-gal vector was first treated with EcoRV to obtain a fragment of 5.8 kb containing two copies of human β-globin MAR sequences, and the fragment was isolated and purified using agarose gel electrophoresis. Subsequently, the fragment containing two copies of MAR was inserted into the opened pCMV-β-gal vector with PmeI treatment. Thus, a complete pCMVMM-β-gal expression vector was obtained.

Figure 8:
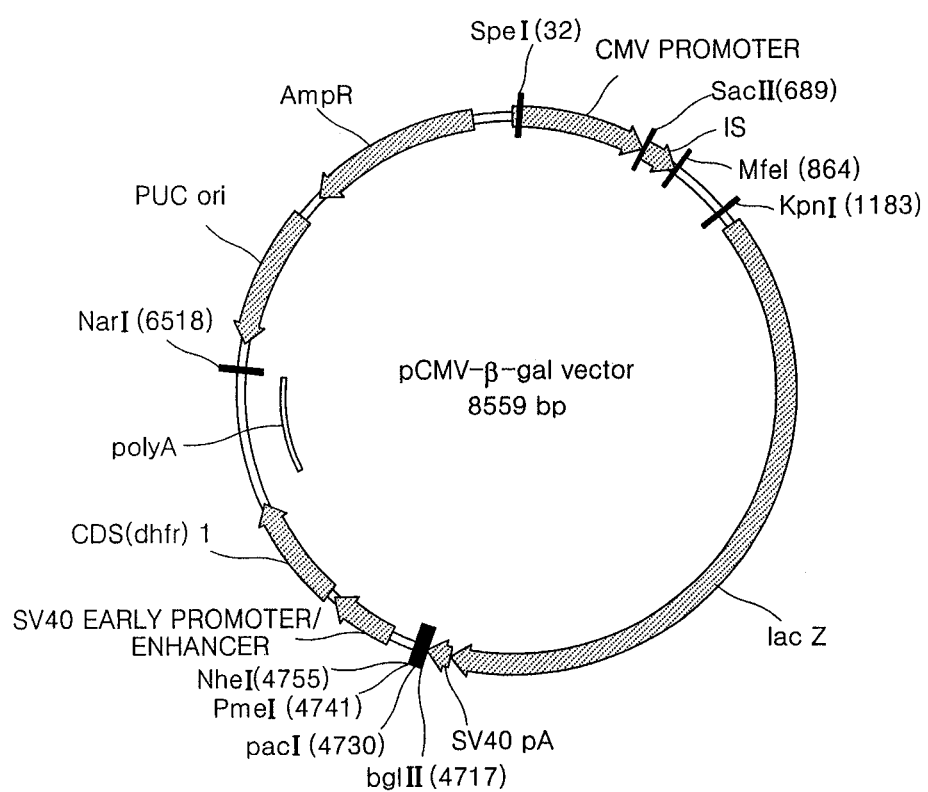
FIG. 8 is a diagram illustrating a pCMV-β-gal vector which contains an operably connected CMV-derived promoter, a lacZ gene, and a SV40 transcription terminator.
Figure 9:
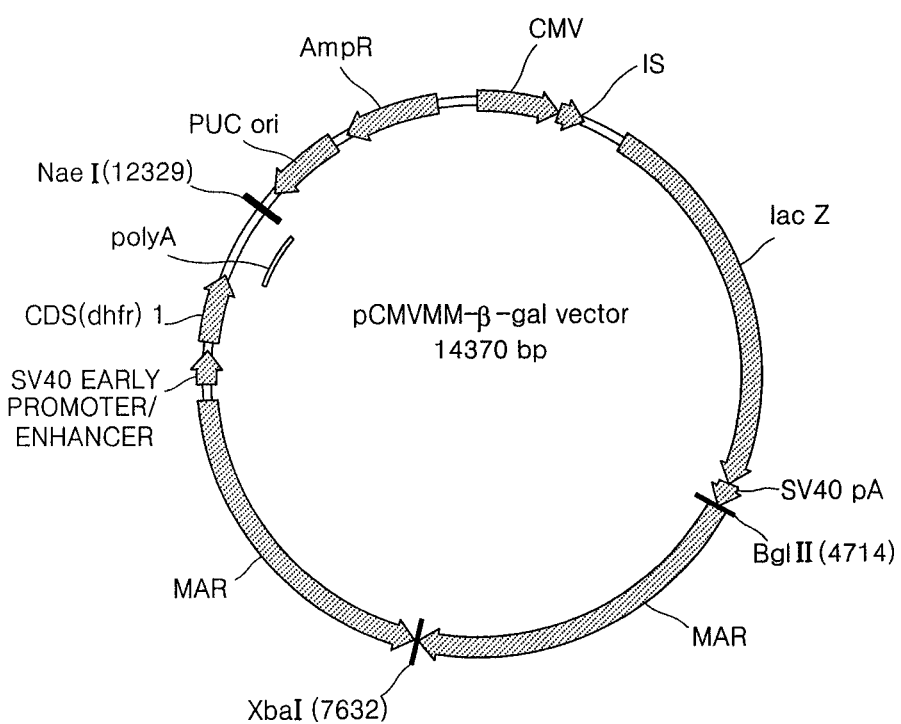
FIG. 9 is a diagram illustrating a pCMVMM-β-gal vector, which has two copies of human β-globin MAR sequences sequentially attached to the 3' terminal of a SV40 transcription terminator that is located downstream to the lacZ gene of a pCMV-β-gal vector.

FIG. 8 is a diagram illustrating the pCMV-β-gal vector, which contains CMV-derived promoter, lacZ gene and SV40 transcription terminator operably connected thereto, while FIG. 9 is a diagram illustrating the pCMVMM-β-gal vector, in which two copies of human β-globin MAR sequences are sequentially connected to the 3' terminal of the SV40 transcription terminator located downstream of the lacZ gene of the pCMV-β-gal vector.

3) Preparation of pCMVMM-IgG Vector Having CMV Promoter, Immunoglobulin Gene and SV40 Transcription Terminator Operably Connected Thereto, and Having Two Copies of Human β-Globin MAR Sequences Connected to the 3' Terminal of SV40 Transcription Terminator.

Using a pCMV-IgG vector containing CMV promoter, human immunoglobulin G gene and SV40 transcription terminator operably connected thereto, an expression vector for animal cell containing two copies of human β-globin MAR sequence at the 3' terminal of the transcription terminator of IgG gene was prepared.

First, the pCMV-IgG vector was treated with PmeI to open the vector, and the opened pCMV-IgG vector was isolated and purified by agarose gel electrophoresis. Next, the opened pCMV-IgG vector was treated with alkaline phosphatase to remove phosphate. After the removal of phosphate, the treatment product was heated at 65° C. for 15 minutes to deactivate the alkaline phosphatase, which was then removed by column chromatography. A pSVMM-β-gal vector was used to insert two copies of human β-globin MAR sequences into the opened pCMV-IgG vector which had been treated as described above. The pSVMM-β-gal vector was treated with EcoRV to obtain a fragment of 5.8 kb containing two copies of human (β-globin MAR sequences, and the fragment was isolated and purified using agarose gel electrophoresis. Subsequently, the fragment containing two copies of MAR was inserted into the opened pCMV-IgG vector with PmeI treatment. Thus, a complete pCMVMM-IgG expression vector was obtained.

Figure 13:
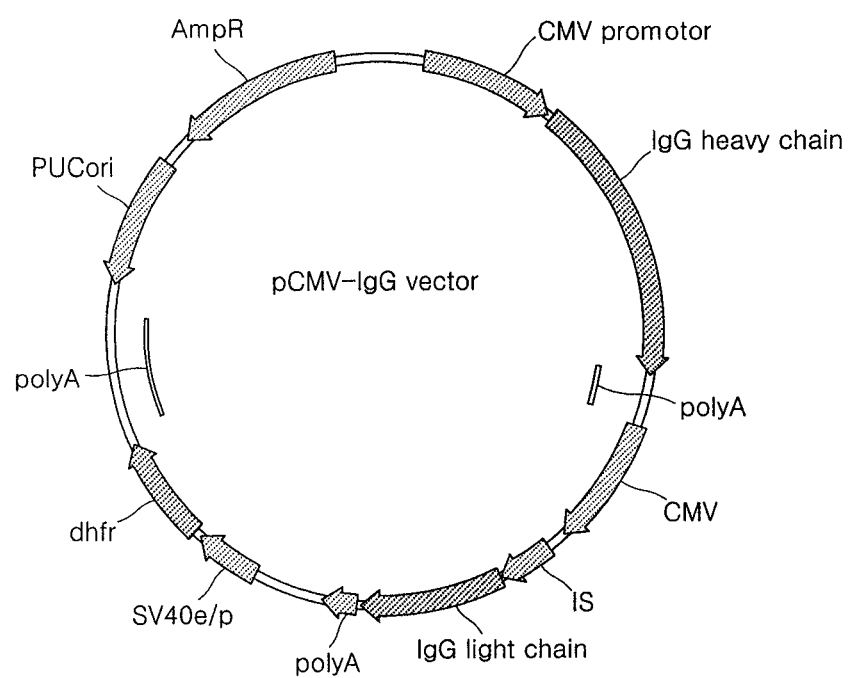
FIG. 13 is a diagram illustrating a pCMV-IgG vector, which contains a CMV-derived promoter and a immunoglobulin gene operably connected thereto, and further contains a dhfr (dihydrofolate reductase) gene as a selective gene.

FIG. 13 is a diagram illustrating the pCMV-IgG vector, which contains CMV-derived promoter and human immunoglobulin G gene operably connected to the promoter. The pCMV-IgG vector contains dhfr (dihydrofolate reductase) gene as a selective gene. In FIG. 13, IS stands for intronic sequence.

FIG. 14 is a diagram illustrating the pCMVMM-IgG vector, in which two copies of human β-globin MAR sequences are sequentially connected to the 3' terminal of transcription terminator of the IgG gene (for heavy chain, BGH polyA; for light chain, SV40 polyA) of the pCMV-IgG vector. The pCMVMM-IgG vector contains dhfr gene as a selective gene. In FIG. 14, IS stands for intronic sequence.

Example 2

Effect of MAR Sequence Attached to the 3' Terminal of Gene on the Expression of the Gene In this example, the pSVM-β-gal vector, pSVMM-β-gal vector, pCMVMM-β-gal vector and pCMVMM-IgG vector prepared in Example 1 were introduced into animal cells, and the animal cells were cultured in order to examine the effect of the human β-globin MAR sequence attached to the 3' terminal of a gene on the expression of the gene. For the control, pSV-β-gal vector (Promega, US), pCMV-β-gal vector and pCMV-Ig vector were used.

1. Transfection of CHO Cell.

(1) Transfection Using DOSPER (Surfactant).

2 μg each of the pSV-β-gal vector, pSVM-β-gal vector and pSVMM-β-gal vector were respectively co-transfected with 33 ng of pSV2neo vector (Clontech, US) into CHO DG44 cell lines (5×10$^5$ cells/well) using a surfactant DOSPER (Roche, Germany), according to the instruction of the manufacturer. In order to perform the co-transfection, the CHO DG44 cell lines were first washed once with a MEM-α medium containing nucleoside but no serum, and then the cell lines were cultured in the same MEM-α medium. After 1 hour, the pSV-β-gal vector, pSVM-β-gal vector and pSVMM-β-gal vector were respectively mixed with the pSV2neo vector containing a selective gene, and then with 5.3 μg of DOSPER (Roche, Germany). Then, the mixtures were allowed to react at ambient temperature for 30 minutes. After the reaction of 30 minutes, the CHO DG44 cell lines that had been cultured in the MEM-α medium were treated with the reaction mixtures, respectively, and the treated cell lines were cultured together with the reaction mixtures for 8 hours. Subsequently, the culture fluid was exchanged with an MEM-α medium containing 10% (v/v) of heat-treated FBS and nucleoside, and the culture was continued for another 36 hours. The transfected CHO DG44 cells were cultured again in a selective medium containing G418 (a MEM-α medium containing 10% of heat-treated FBS, 850 μg/ml of G418 and nucleoside) for about 3 weeks, and the cell line having resistance to G418 was selected.

The obtained cell lines, that is, the cell lines transfected with the pSV-β-gal vector, pSVM-β-gal vector and pSVMM-β-gal vector, respectively, and having resistance to G418 were assayed, in order to examine the frequency of cells expressing β-galactosidase and the amount of expressed β-galactosidase.

(2) Transfection Using Calcium Phosphate.

2 μg each of the pSV-β-gal vector, pSVMM-β-gal vector, pCMV-β-gal vector and pCMVMM-β-gal vector were respectively co-transfected with 500 ng of pSV2neo vector (Clontech, US) into CHO DG44 cell lines (5×10$^5$ cells/well) using calcium phosphate. In order to perform the co-transfection, the CHO DG44 cell lines were first washed once with a MEM-α medium containing nucleoside and 1% of FBS, and then the cell lines were cultured in the same MEM-α medium. After 1 hour, the pSV-β-gal vector, pSVMM-β-gal vector, pCMV-β-gal vector and pCMVMM-β-gal vector were respectively mixed with the pSV2neo vector containing a selective gene, and then with calcium phosphate to form precipitates. The CHO DG44 cell lines that had been cultured in the MEM-α medium were treated with the previously formed precipitates for 4 hours, and then with a 10% glycerol solution. After the 1-minute treatment, the glycerol solution was completely removed, subsequently the culture fluid was exchanged with an MEM-α medium containing 10% (v/v) of heat-treated FBS and nucleoside, and the culture was continued for another 36 hours. The transfected CHO DG44 cells were cultured again in a selective medium containing G418 (a MEM-α medium containing 10% heat-inactivated FBS, 850 μg/ml of G418 and nucleoside) for about 3 weeks, and the cell line having resistance to G418 was selected.

The obtained cell lines, that is, the cell lines transfected with the pSV-β-gal vector, pSVMM-β-gal vector, pCMV-β-gal vector and pCMVMM-β-gal vector, respectively, and having resistance to G418 were assayed, in order to examine the frequency of cells expressing β-galactosidase and the amount of expressed β-galactosidase.

In addition, 2.5 μg of each of the pCMV-IgG vector and the pCMVMM-IgG vector were respectively introduced into CHO DG44 cell lines (5×10$^5$ cells/well) using calcium phosphate. In order to perform the introduction, the CHO DG44 cell lines were first washed once with a MEM-α medium containing nucleoside and 1% of FBS, and then the cell lines were cultured in this MEM-α medium. After 1 hour, the pCMV-IgG vector and the pCMVMM-IgG vector were respectively mixed with calcium phosphate to form precipitates. The CHO DG44 cell lines that had been cultured in the MEM-α medium were respectively treated with the precipitates for 4 hours, and then with a 10% glycerol solution for 1 minute. After the treatment of 1 minute, the glycerol solution was completely removed, subsequently the culture fluid was exchanged with an MEM-α medium containing 10% (v/v) of heat-treated FBS and nucleoside, and the culture was continued for another 72 hours. After the 72-hour culture, the transfected CHO DG44 cells were cultured in a 6-well plate using a selective medium (SFM4-CHO medium (Hyclone, US)) in which only a cell line containing dfhr gene can grow. Subsequently, the amounts of IgG expression in the transfected. CHO DG44 cell lines were examined.

2. Investigation of Amount of β-Galactosidase Expression and the Frequency of β-Galactosidase Positive Cells in Cell Lines Respectively Transfected with pSVM-β-Gal Vector and pSVMM-β-Gal Vector and Having Resistance to G418.

In transient CHO DG44 cells transfected with the pSV-β-gal vector, pSVM-β-gal vector and pSVMM-β-gal vector, respectively, the amounts of β-galactosidase expression were measured through an analysis of β-galactosidase enzyme activity. First, the cell lines were transfected, and after 48 hours, the CHO DG44 cell lines transfected with the pSV-β-gal vector, pSVM-β-gal vector and pSVMM-β-gal vector, respectively, were washed twice with 1×PBS, and the cells were separated from the culture vessel using a 0.25% trypsin solution. The separated cells were washed twice with PBS, and then a lysis buffer (0.25 M Tris-HCl containing 0.1% of Nonidet P40, pH 8.0) was added to the cells in an amount of 200 μl per 5×10$^6$ cells. The cell-buffer mixtures were allowed to react at 4° C. for 30 minutes. During the reaction of 30 minutes, the cell-buffer mixtures were mixed using vortex every 10 minutes. After the reaction, the cell-buffer mixtures were centrifuged at 4° C. at 13,000 rpm for 10 minutes, and then the supernatants were transferred to new tubes. The obtained supernatants, that is, the cell lysates, were subjected to an analysis for β-galactosidase enzyme activity using a β-Gal assay kit (Invitrogen, US) according to the instructions of the manufacturer. 10 μl of each of the cell lysates was added to a 96-well plate for EIA, and then 50 μl of a 1× cleavage solution (60 mM $Na_2HPO_4.7H_2O$, 40 mM $NaH_2PO_4.H_2O$, 10 mM KCl, 1 mM $MgSO_4.7H_2O$, pH 7.0) and 17 ml of an ONPG solution (concentration: 4 mg/ml) were added thereto, allowing the mixture to react at 37° C. for 30 minutes. 125 μl of a reaction stop solution was added to terminate the reaction, and then the absorbance of the reaction mixture was measured at 420 nm. The total amounts of protein in the cell lysates were measured according to a bicinchoninic acid (BCA) method, and the β-galactosidase enzyme activities were normalized to the activity obtainable with a constant amount of protein for the analysis.

Figure 4:
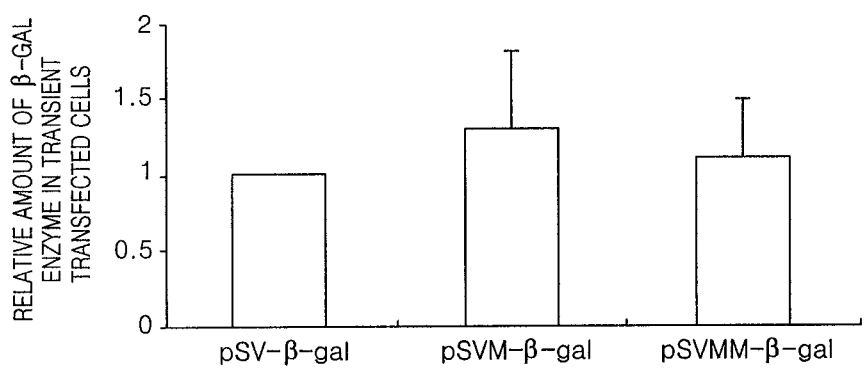
FIG. 4 is a graph indicating results of an assay for β-galactosidase enzyme activity in CHO DG44 cell lines that are transfected with pSV-β-gal vector, pSVM-β-gal vector and pSVMM-β-gal vector, respectively, in a transient state.

FIG. 4 is a graph indicating analysis results of β-galactosidase enzyme activity in CHO DG44 cell lines in a transient state, which are transfected with the pSV-β-gal vector, pSVM-β-gal vector and pSVMM-β-gal vector, respectively. As shown in FIG. 4, the β-galactosidase expression did not increase in the case of transfection with one copy of MAR sequence as well as the case of transfection with two copies of MAR sequences. It can be seen from the results that, as previously reported, the MAR element does not increase expression of a gene in a transiently transfected cell, even though the gene is connected to the MAR element.

Subsequently, the β-galactosidase enzyme activities in cell lines that were transfected with the pSV-β-gal vector, pSVM-β-gal vector and pSVMM-β-gal vector, respectively, and had resistance to G418, were analyzed. First, 2 μg of the pSV-β-gal vector, pSVM-β-gal vector and pSVMM-β-gal vector were co-transfected with 33 ng of a pSV2neo vector (Clontech, US) into CHO DG44 cell lines ($5 \times 10^5$ cells/well) using a surfactant, DOSPER (Roche, Germany), according to the instructions of the manufacturer. After 36 hours of the co-transfection, the cell lines were cultured in a selective medium containing G418 (a MEM-α medium containing 10% of heat-treated FBS, 850 μg/ml of G418 and nucleoside) for about 3 weeks to obtain CHO DG44 cell lines having resistance to G418. The amounts of β-galactosidase expression were measured in the CHO DG44 cell lines having resistance to G418 through analysis of β-galactosidase enzyme activity.

Figure 5:
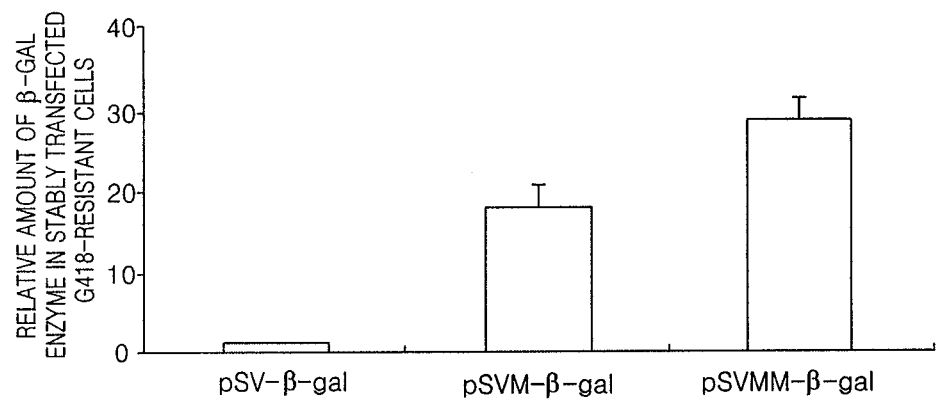
FIG. 5 is a graph indicating results of an assay for β-galactosidase enzyme activity in CHO DG44 cell lines that are transfected with pSV-β-gal vector, pSVM-β-gal vector and pSVMM-β-gal vector, respectively, and have resistance to G418.

FIG. 5 is a graph indicating analysis results of β-galactosidase enzyme activity in CHO DG44 cell lines that were transfected with pSV-β-gal vector, pSVM-β-gal vector and pSVMM-β-gal vector, respectively, and had resistance to G418. As shown in FIG. 5, the amount of β-galactosidase expression increased 18- to 29-fold compared with the control, in the CHO DG44 cell lines having resistance to G418, by introducing the MAR sequence to the 3' terminal of polyadenylation signal. In particular, when two copies of MAR sequences were introduced, the increasing effect was enhanced by about 60% compared with the case where one copy of MAR sequence was introduced.

Then the frequency of β-galactosidase positive cells in the previously obtained CHO DG44 cell lines that were transfected with the pSV-β-gal vector, pSVM-β-gal vector and pSVMM-β-gal vector, respectively, and had resistance to G418, were measured using a β-gal staining method. First, the cells cultured in a 6-well plate using a selective medium (a MEM-α medium containing 10% of heat-treated FBS, 850 μg/ml of G418 and nucleoside) were washed twice with 1×PBS and were separated from the culture vessel using a 0.25% trypsin solution. The separated cells were treated with the selective medium to deactivate trypsin, subsequently centrifuged to remove trypsin and were washed twice with 1×PBS. After the washing, the cells were treated with a fixing solution comprising 2% formaldehyde and 0.2% glutaraldehyde at 4° C. for 10 minutes to fix the cells and were washed twice with PBS. Then, the cells were stained with ONPG, which is coloration product obtained by treating X-Gal, a substrate for β-Gal enzyme. As are suit of the staining, positive cells turned blue.

Figure 6:
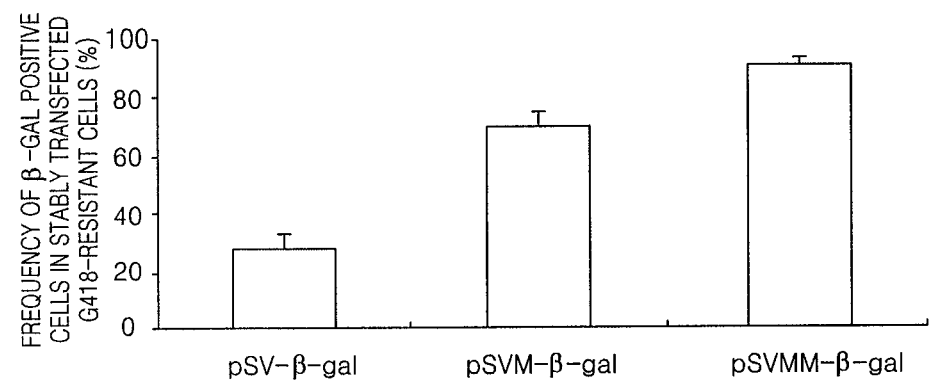
FIG. 6 is a graph indicating the frequency of β-galactosidase positive cells that are obtained as a result of ONPG (ortho-nitrophenyl-β-D-galactopyranoside) staining of CHO DG44 cell lines which are transfected with a pSV-β-vector, a pSVM-β-gal vector and a pSVMM-β-gal vector, respectively, and have resistance to G418.

FIG. 6 is a graph indicating the frequency of β-galactosidase positive cells when the previously obtained CHO DG44 cell lines which were transfected with the pSV-β-gal vector, pSVM-β-gal vector and pSVMM-β-gal vector, respectively, and having resistance to G418 were stained with ONPG. As shown in FIG. 6, the frequency of β-galactosidase positive cells increased, as the MAR sequence was introduced at the 3' terminal of transcription termination region, that is, polyadenylation signal of a gene. This implies that the MAR sequence introduced at the 3' terminal of the polyadenylation signal increases the expression of the gene upstream thereto. Also, as shown in FIG. 6, when two copies of MAR sequences were introduced, the frequency of β-galactosidase positive cells significantly increased (about 90%), compared with the case where one copy of MAR sequence was introduced (about 70%).

Figure 7:
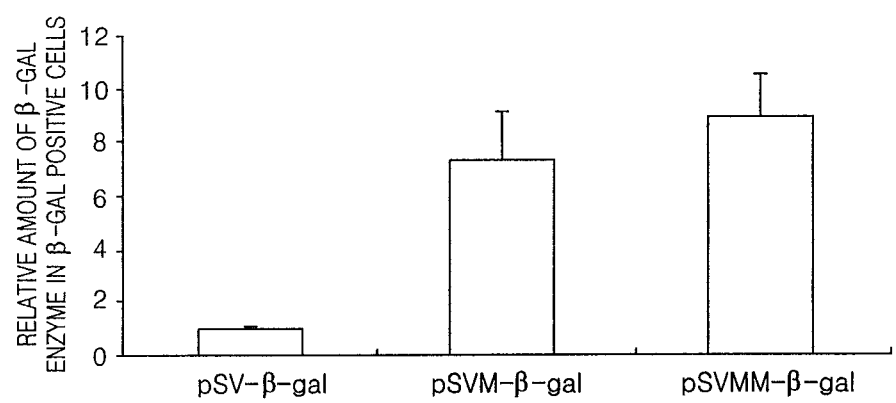
FIG. 7 is a graph indicating amounts of β-galactosidase expression, which are calculated on the basis of the frequency of β-galactosidase positive cells shown in FIG. 6.

FIG. 7 is a graph indicating the amounts of β-galactosidase expression presented in FIG. 5, which were recalculated on the basis of the frequency of β-galactosidase positive cells. As shown in FIG. 7, the amount of β-galactosidase expression per positive cell unit increased 7.4- to 8.9-fold compared with the control, as a result of introducing human β-globin MAR sequence to the 3' terminal of the β-galactosidase gene. In particular, the amount of β-galactosidase expression increased by about 20% in the case of introducing two copies of MAR sequences, compared with the case of introducing only one copy of MAR sequence.

3. Investigation of the Amount of β-Galactosidase Expression and the Frequency of β-Galactosidase Positive Cells in Cell Line Having pCMVMM-β-Gal Vector Introduced and Having Resistance to G418.

First, the amounts of β-galactosidase expression in the cell lines which were transfected with the pCMV-β-gal vector and pCMVMM-β-gal vector, respectively, and had resistance to G418, were measured through analysis for β-galactosidase enzyme activity. First, the G418-resistant CHO DG44 cells that had been cultured in a selective medium for about 3 weeks after transfection with the pCMV-β-gal vector and pCMVMM-β-gal vector, respectively were washed two times with 1×PBS, and the cells were separated from the culture vessel using a 0.25% trypsin solution. The separated cells were washed two times with PBS, then 200 μl of a lysis buffer (0.25 M Tris-HCl pH 8.0, 0.1% Nonidet P40) was added per $10^6$ cells, and the cell-buffer mixtures were allowed to react at 4° C. for 30 minutes. During the reaction time of 30 minutes, the cell-buffer mixtures were mixed using vortex every 10 minutes. After the reaction, the reaction mixtures were centrifuged at 4° C. and at 13,000 rpm for 10 minutes, and the supernatants were transferred to new tubes. The obtained supernatants, that is, the cell lysates, were then subjected to analysis for β-galactosidase enzyme activity using a β-Gal assay kit (Invitrogen, US), according to the instructions of the manufacturer. 10 μl of each of the cell lysate was added to a 96-well plate for EIA, and then 50 μl of a 1× cleavage solution (60 mM $Na_2HPO_4.7H_2O$, 40 mM $NaH_2PO_4.H_2O$, 10 mM KCl, 1 mM $MgSO_4.7H_2O$, pH 7.0) and 17 μl of an ONPG solution (concentration: 4 mg/ml) were added thereto, allowing the mixture to react at 37° C. for 30 minutes. 125 μl of a reaction stop solution was added to terminate the reaction, and then the absorbance of the reaction mixture was measured at 420 nm. The total amount of protein in the cell lysates was measured according to the bicinchoninic acid (BCA) method, and the β-galactosidase enzyme activity was normalized to the activity obtainable with a constant amount of protein for the analysis.

Figure 10:
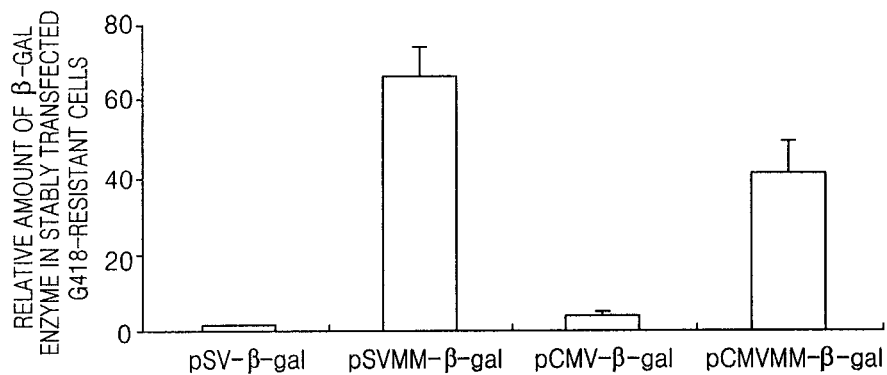
FIG. 10 is a graph indicating results of an assay for β-galactosidase enzyme activity against CHO DG44 cell lines that are transfected with pCMV-β-gal vector and pCMVMM-β-gal vector, respectively, and have resistance to G418.

FIG. 10 is a graph indicating analysis results of β-galactosidase enzyme activity in the CHO DG44 cell lines that were transfected with the pCMV-β-gal vector and pCMVMM-β-gal vector, respectively, and had resistance to G418. As shown in FIG. 10, the amounts of β-galactosidase expression, which was connected to the CMV-derived promoter, in the CHO DG44 cell lines having resistance to G418 increased about 6.3-fold compared with the control vector, as two copies of MAR sequences were introduced at the 3' terminal of the polyadenylation signal.

Next, the frequency of β-galactosidase positive cells was investigated using the β-gal staining method. First, cells cultured in a 6-well plate using a selective medium (a MEM-α medium containing 10% of heat-treated FBS, 850 μg/ml of G418 and nucleoside) were washed twice with 1×PBS and were separated from the culture vessel using a 0.25% trypsin solution. The separated cells were treated with the selective medium to deactivate trypsin, subsequently centrifuged to remove trypsin, and then washed twice with 1×PBS. After the washing, the cells were treated with a fixing solution comprising 2% formaldehyde and 0.2% glutaraldehyde at 4° C. for 10 minutes to fix the cells and were washed twice with PBS. Then the cells were stained with ONPG, which is a coloration product obtained by treating X-Gal, a substrate for β-Gal enzyme. As a result of the staining, the positive cells turned blue.

Figure 11:
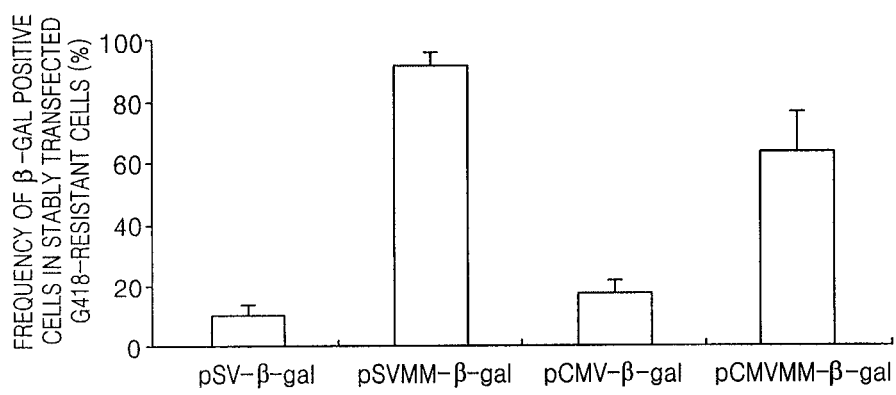
FIG. 11 is a graph indicating the frequency of β-galactosidase positive cells that are obtained as a result of ONPG staining of CHO DG44 cell lines which are transfected with a pCMV-β-gal vector and a pCMVMM-β-gal vector, respectively, and have resistance to G418.

FIG. 11 is a graph indicating the frequency of β-galactosidase positive cells, which were obtained as a result of staining the CHO DG44 cell lines, that were transfected with the pCMV-β-gal vector and the pCMVMM-β-gal vector, respectively, and had resistance to G418, with ONPG. As shown in FIG. 11, the frequency of β-galactosidase positive cells increased about 3.1-fold as MAR sequences were introduced at the 3' terminal of the transcription termination region, that is, the polyadenylation signal, of the gene. This implies that the MAR sequence introduced at the 3' terminal of the polyadenylation signal increased the gene expression, even in the case where the gene located upstream to the MAR sequence uses a CMV-derived promoter instead of SV40 promoter.

Figure 12:
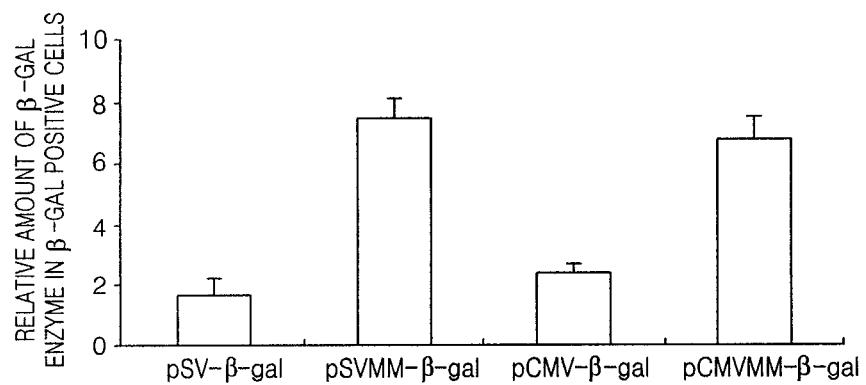
FIG. 12 is a graph indicating amounts of a β-galactosidase expression, which are calculated on the basis of the frequency of β-galactosidase positive cells shown in FIG. 11.

FIG. 12 is a graph indicating amounts of β-galactosidase expression presented in FIG. 10, which were recalculated on the basis of the frequency of β-galactosidase positive cells. As shown in FIG. 12, the amounts of β-galactosidase expression per positive cell unit increased about 2.2-fold compared with the control, when human β-globin MAR sequence is introduced at the 3' terminal of gene.

4. Investigation of the Amount of IgG Expression in Cell Line Having pCMVMM-IgG Vector Introduced and Cultured in a Medium for Screening dhfr Gene CHO DG44 cells were transfected with the pCMV-IgG vector and the pCMVMM-IgG vector, respectively, and then the transfected CHO cells were cultured in a selective medium (SFM4-CHO medium (Hyclone, US) containing 5% heat-inactivated and dialyzed FBS) in which only those cell lines containing dhfr gene can grow, for 2 weeks. Subsequently, these cell lines were inoculated onto a 6-well plate using 3 types of selective media containing MTX at a concentration of $7\times10^5$ cells/ml, cultured for 3 days, and then the amount of IgG expression in the culture fluid was measured. The selective media used contained 0 nM, 25 nM, 50 nM and 100 nM of MTX, respectively.

Figure 15:
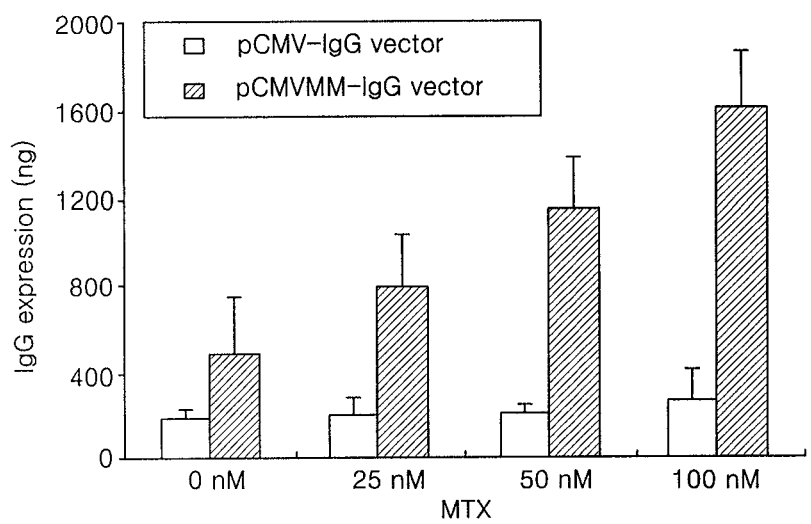
FIG. 15 is a graph indicating results of a IgG expression level measurement performed after transfecting CHO DG44 cell lines with a pCMVMM-IgG expressing vector according to an embodiment of the present invention, and a pCMV-IgG vector, which is a control vector, and then adding MTX to the transfected cell lines to induce amplification of the genes.

FIG. 15 is a graph indicating amounts of IgG expression measured after transfecting CHO DG44 cell lines with the pCMVMM-IgG expression vector according to an embodiment of the present invention and a control vector pCMV-IgG expression vector, respectively, and then inducing gene amplification by adding MTX to the transfected cell lines. As shown in FIG. 15, the amount of IgG expression increased, as two copies of MAR sequences were introduced at the 3' terminal of the polyadenylation signal. Further, as the concentration of MTX increased, the rate of increase in the amount of IgG expression was higher for the pCMVMM-IgG expression vector compared with the control pCMV-IgG vector. When treated with 100 nM of MTX, the amount of IgG expression in the cells containing the pCMVMM-IgG vector increased about 6-fold, compared with the cells containing the control pCMV-IgG vector.

Figure 16:
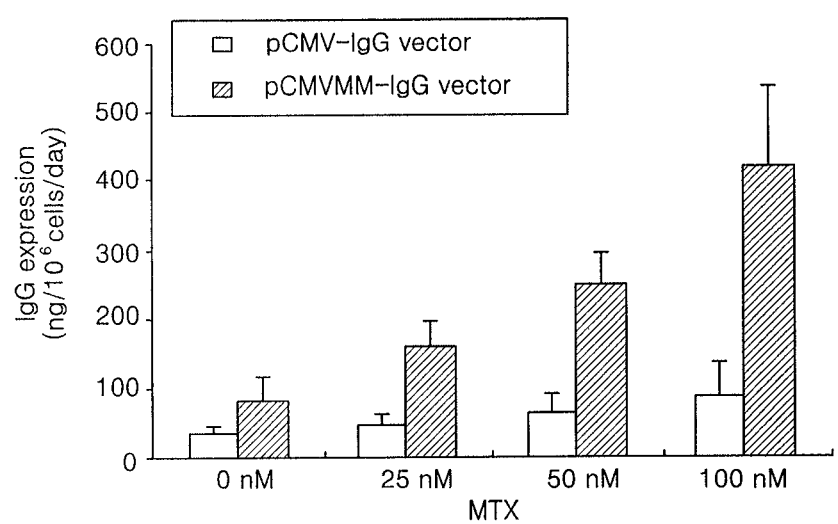
FIG. 16 is a graph indicating results comparing the expression levels of IgG in the culture fluid obtained from the experiment of FIG. 15, which are normalized to expression levels of IgG obtainable from $10^6$ cells for 24 hours.

FIG. 16 is a graph indicating results of comparison of the amounts of IgG expression in the culture fluid obtained in the experiment of FIG. 15, which were normalized to the expression amount values produced by $10^6$ cells for 24 hours. As shown in FIG. 16, in the case of the pCMVMM-IgG vector, when the cells were treated with 100 nM of MITX, the amount of IgG expression increased about 5-fold, compared with the cell line containing the control pCMV-IgG vector. It can be also seen from FIG. 16 that as the MTX concentration is increased, the rate of increase in the amount of IgG expressional so increased. This implies that during the process of gene amplification, cells containing the pCMVMM-IgG vector are amplified and express the IgG gene more efficiently than the cells containing the pCMV-IgG vector.

From the results of the Examples of the present invention as described above, it can be seen that when a human β-globin MAR sequence is introduced at the 3' terminal of a transcription termination signal of a gene, expression of an upstream gene located next to a promoter including SV40 promoter and CMV promoter is significantly enhanced. Introduction of one copy of a human β-globin MAR sequence led to a significant increase in the expression of the upstream gene, and in particular, introduction of two copies of human β-globin MAR sequences led to further enhancement in the increasing effect induced by the introduction of one copy of the MAR sequence. This occurrence is believed to be caused by the notable reduction of the position effects by the introduced MAR sequence on adjacent nucleic acid sequences present in the host cell, but the present invention is not intended to be limited to this specific mechanism.

INDUSTRIAL APPLICABILITY

The expression vector for an animal cell according to an embodiment of the present invention can be used to significantly increase expression of foreign genes in animal cells.

The gene expression method according to an embodiment of the present invention can be used to express genes in animal cells easily with high efficiency.

The invention claimed is:

1. An expression vector for an animal cell comprising
   a promoter,
   a cloning site or a polynucleotide encoding a foreign gene product, and
   a transcription terminator,
   all of which are operably connected to each other within the expression vector, wherein the vector comprises a polynucleotide containing nucleotides 4161 to 10134 of SEQ ID NO:2, in which two copies of human β-globulin MAR sequences are connected adjacently to each other, wherein said two copies of human β-globin matrix attachment region (MAR) are located at the 3' terminal of the transcription terminator.

2. The expression vector of claim 1, wherein the promoter is SV40 early promoter or CMV promoter.

3. The expression vector of claim 1, wherein the polynucleotide encoding the foreign product is a gene encoding lacZ, immunoglobulin, granulocyte colony-stimulating factor (GCSF) or erythropoietin (EPO).

4. The expression vector of claim 1, wherein the transcription terminator is SV40 virus transcription terminator.

5. The expression vector of claim 1, wherein the expression vector is SEQ ID NO: 2 or a pCMVMM-IgG expression vector having the vector map shown in FIG. 14.

6. A method of expressing a foreign gene, comprising transfecting an animal cell with the expression vector according to claim 1 which comprises a polynucleotide encoding the foreign gene product, and culturing the transfected animal cell.

7. The method of claim 6, wherein the animal cell is selected from the group consisting of Chinese hamster ovary (CHO) cells, Baby hamster kidney (BHK) cells, NS0 cells and human cells.

* * * * *

SEQUENCE LISTING

<160> NUMBER OF SEQ ID NOS: 7

<210> SEQ ID NO 1
<211> LENGTH: 9813
<212> TYPE: DNA
<213> ORGANISM: Artificial Sequence
<220> FEATURE:
<223> OTHER INFORMATION: Polynucleotide sequence of pSVM-beta-gal expression vector

<400> SEQUENCE: 1

| | | | | | |
|---|---|---|---|---|---|
| gcgcagcacc | atggcctgaa | ataacctctg | aaagaggaac | ttggttaggt | accttctgag | 60 |
| gcggaaagaa | ccagctgtgg | aatgtgtgtc | agttagggtg | tggaaagtcc | ccaggctccc | 120 |
| cagcaggcag | aagtatgcaa | agcatgcatc | tcaattagtc | agcaaccagg | tgtggaaagt | 180 |
| ccccaggctc | cccagcaggc | agaagtatgc | aaagcatgca | tctcaattag | tcagcaacca | 240 |
| tagtcccgcc | cctaactccg | cccatcccgc | cctaactccc | gccagttccg | cccattctc | 300 |
| cgccccatgg | ctgactaatt | tttttattt | atgcagaggc | cgaggccgcc | tcggcctctg | 360 |
| agctattcca | gaagtagtga | ggaggctttt | ttggaggcct | aggcttttgc | aaaaagcttg | 420 |
| ggatctctat | aatctcgcgc | aacctatttt | ccctcgaac | acttttaag | ccgtagataa | 480 |
| acaggctggg | acacttcaca | tgagcgaaaa | atacatcgtc | acctgggaca | tgttgcagat | 540 |
| ccatgcacgt | aaactcgcaa | gccgactgat | gccttctgaa | caatggaaag | gcattattgc | 600 |
| cgtaagccgt | ggcggtctgg | taccggtggg | tgaagaccag | aaacagcacc | tcgaactgag | 660 |
| ccgcgatatt | gcccagcgtt | tcaacgcgct | gtatggcgag | atcgatcccg | tcgttttaca | 720 |
| acgtcgtgac | tgggaaaacc | ctggcgttac | ccaacttaat | cgccttgcag | cacatccccc | 780 |
| tttcgccagc | tggcgtaata | gcgaagaggc | ccgcaccgat | cgcccttccc | aacagttgcg | 840 |
| cagcctgaat | ggcgaatggc | gctttgcctg | gtttccggca | ccagaagcgg | tgccggaaag | 900 |
| ctggctggag | tgcgatcttc | ctgaggccga | tactgtcgtc | gtcccctcaa | actggcagat | 960 |
| gcacggttac | gatgcgccca | tctacaccaa | cgtgacctat | cccattacgg | tcaatccgcc | 1020 |
| gtttgttccc | acggagaatc | cgacgggttg | ttactcgctc | acatttaatg | ttgatgaaag | 1080 |
| ctggctacag | gaaggccaga | cgcgaattat | ttttgatggc | gttaactcgg | cgtttcatct | 1140 |
| gtggtgcaac | gggcgctggg | tcggttacgg | ccaggacagt | cgtttgccgt | ctgaatttga | 1200 |
| cctgagcgca | tttttacgcg | ccggagaaaa | ccgcctcgcg | gtgatggtgc | tgcgctggag | 1260 |
| tgacggcagt | tatctggaag | atcaggatat | gtggcggatg | agcggcattt | tccgtgacgt | 1320 |
| ctcgttgctg | cataaaccga | ctacacaaat | cagcgatttc | catgttgcca | ctcgctttaa | 1380 |
| tgatgatttc | agccgcgctg | tactggaggc | tgaagttcag | atgtgcggcg | agttgcgtga | 1440 |
| ctacctacgg | gtaacagttt | ctttatggca | gggtgaaacg | caggtcgcca | gcggcaccgc | 1500 |
| gcctttcggc | ggtgaaatta | tcgatgagcg | tggtggttat | gccgatcgcg | tcacactacg | 1560 |
| tctgaacgtc | gaaaacccga | aactgtggag | cgccgaaatc | ccgaatctct | atcgtgcggt | 1620 |
| ggttgaactg | cacaccgccg | acggcacgct | gattgaagca | gaagcctgcg | atgtcggttt | 1680 |
| ccgcgaggtg | cggattgaaa | atggtctgct | gctgctgaac | ggcaagccgt | tgctgattcg | 1740 |
| aggcgttaac | cgtcacgagc | atcatcctct | gcatggtcag | gtcatggatg | agcagacgat | 1800 |
| ggtgcaggat | atcctgctga | tgaagcagaa | caactttaac | gccgtgcgct | gttcgcatta | 1860 |
| tccgaaccat | ccgctgtggt | acacgctgtg | cgaccgctac | ggcctgtatg | tggtggatga | 1920 |
| agccaatatt | gaaacccacg | gcatggtgcc | aatgaatcgt | ctgaccgatg | atccgcgctg | 1980 |

-continued

```
gctaccggcg atgagcgaac gcgtaacgcg aatggtgcag cgcgatcgta atcacccgag    2040
tgtgatcatc tggtcgctgg ggaatgaatc aggccacggc gctaatcacg acgcgctgta    2100
tcgctggatc aaatctgtcg atccttcccg cccggtgcag tatgaaggcg gcggagccga    2160
caccacggcc accgatatta tttgcccgat gtacgcgcgc gtggatgaag accagccctt    2220
cccggctgtg ccgaaatggt ccatcaaaaa atggctttcg ctacctggag agacgcgccc    2280
gctgatcctt tgcgaatacg cccacgcgat gggtaacagt cttggcggtt tcgctaaata    2340
ctggcaggcg tttcgtcagt atccccgttt acagggcggc ttcgtctggg actgggtgga    2400
tcagtcgctg attaaatatg atgaaaacgg caacccgtgg tcggcttacg gcggtgattt    2460
tggcgatacg ccgaacgatc gccagttctg tatgaacggt ctggtctttg ccgaccgcac    2520
gccgcatcca gcgctgacgg aagcaaaaca ccagcagcag tttttccagt tccgtttatc    2580
cgggcaaacc atcgaagtga ccagcgaata cctgttccgt catagcgata acgagctcct    2640
gcactggatg gtggcgctgg atggtaagcc gctggcaagc ggtgaagtgc ctctggatgt    2700
cgctccacaa ggtaaacagt tgattgaact gcctgaacta ccgcagccgg agagcgccgg    2760
gcaactctgg ctcacagtac gcgtagtgca accgaacgcg accgcatggt cagaagccgg    2820
gcacatcagc gcctggcagc agtggcgtct ggcgaaaaac ctcagtgtga cgctccccgc    2880
cgcgtcccac gccatcccgc atctgaccac cagcgaaatg gattttgca tcgagctggg    2940 taataagcgt tggcaattta accgccagtc aggctttctt tcacagatgt ggattggcga    3000
taaaaaacaa ctgctgacgc cgctgcgcga tcagttcacc cgtgcaccgc tggataacga    3060
cattggcgta agtgaagcga cccgcattga ccctaacgcc tgggtcgaac gctggaaggc    3120
ggcgggccat taccaggccg aagcagcgtt gttgcagtgc acggcagata cacttgctga    3180
tgcggtgctg attacgaccg ctcacgcgtg gcagcatcag gggaaaacct tatttatcag    3240
ccggaaaacc taccggattg atggtagtgg tcaaatggcg attaccgttg atgttgaagt    3300
ggcgagcgat acaccgcatc cggcgcggat tggcctgaac tgccagctgg cgcaggtagc    3360
agagcgggta aactggctcg gattagggcc gcaagaaaac tatcccgacc gccttactgc    3420
cgcctgtttt gaccgctggg atctgccatt gtcagacatg tatacccgt acgtcttccc    3480 gagcgaaaac ggtctgcgct gcgggacgcg cgaattgaat tatggcccac accagtggcg    3540
cggcgacttc cagttcaaca tcagccgcta cagtcaacag caactgatgg aaaccagcca    3600
tcgccatctg ctgcacgcgg aagaaggcac atggctgaat atcgacggtt ccatatggg    3660 gattggtggc gacgactcct ggagcccgtc agtatcggcg gaattccagc tgagcgccgg    3720
tcgctaccat taccagttgg tctggtgtca aaaataataa taaccgggca ggccatgtct    3780
gcccgtattt cgcgtaagga atccattat gtactattta aaaaacacaa acttttggat    3840
gttcggttta ttctttttct tttactttt tatcatggga gcctacttcc cgttttccc    3900 gatttggcta catgacatca accatatcag caaaagtgat acgggtatta ttttgccgc    3960 tatttctctg ttctcgctat tattccaacc gctgtttggt ctgcttttctg acaaactcgg    4020 aacttgttta ttgcagctta taatggttac aaataaagca atagcatcac aaatttcaca    4080
aataaagcat ttttttcact gcattctagt tgtggtttgt ccaaactcat caatgtatct    4140
tatcatgtct ggatccagat cttagggcgc cctgcagttc ttcctcttta ggttctcctt    4200
tatggaatct tctgtactga tggccatgtc ctttaactac tatgtagata tctgctacta    4260
cctgtattat gcctctacct ttattagcag agttatctga actgttggca tgacaatcat    4320
ttgttaatat gacttgcctt tccttttttct gctattcttg atcaaatggc tcctctttct    4380
```

```
tgctcctctc atttctcctg ccttcacttg gacgtgcttc acgtagtctg tgcttatgac    4440
tggattaaaa attgatatgg acttatccta atgttgttcg tcataatatg ggttttatgg    4500
tccattatta tttcctatgc attgatctgg agaaggcttc aatccttttta ctctttgtgg   4560 aaaatatctg taaaccttct ggttcactct gctatagcaa tttcagttta ggctagtaag    4620
catgaggatg cctccttctc tgattttttcc cacagtctgt tggtcacaga ataacctgag   4680
tgattactga tgaaagagtg agaatgttat tgatagtcac aatgacaaaa aacaaacaac    4740
tacagtcaaa atgtttctct ttttattagt ggttatattt cctgacctat atctggcagg    4800
actctttaga gaggtagctg aagctgctgt tatgaccact agagggaaga agataacctgt   4860 ggagctaatg gtccaagatg gtggagcccc aagcaaggaa gttgttaagg agccttttg    4920 attgaaggtg ggtgccccca ccttacaggg acaggacatc tggatactcc tcccagtttc    4980
tccagtttcc cttttttccta atatatctcc tgataaaatg tctatactca cttccccatt   5040
tctaataata aagcaaaggc tagtagtaa gacatcacct tgcattttga aaatgccata    5100
gactttcaaa attatttcat acatcggtct ttctttatttt caagagtcca gaaatggcaa    5160
cattaccttt gattcaatgt aatggaaaga gctctttcaa gagacagaga aaagaataat    5220
ttaatttctt tccccacacc tccttccctg tctcttaccc tatcttcctt ccttctaccc    5280
tccccatttc tctctctcat ttctcagaag tatattttga aaggattcat agcagacagc    5340
taaggctggt tttttctaag tgaagaagtg atattgagaa ggtagggttg catgagccct    5400
ttcagttttt tagtttatat acatctgtat tgttagaatg ttttataata taaataaaat    5460
tatttctcag ttatatacta gctatgtaac ctgtggatat ttccttaagt attacaagct    5520
atacttaact cacttggaaa actcaaataa ataccotgctt catagttatt aataaggatt    5580
aagtgagata atgccctata agattcctat taataacaga taaatacata cacacacaca    5640
cacattgaaa ggattcttac tttgtgctag gaactataat aagttcattg atgcattata    5700
tcattaagtt ctaatttcaa cactagaagg caggtattat ctaaatttca tactggatac    5760
ctccaaactc ataaagataa ttaaattgcc ttttgtcata tatttattca aaagggtaac    5820
tcaaactatg gcttgtctaa ttttatatat caccctactg aacatgaccc tattgtgata    5880
ttttataaaa ttatctcaag ttattatgag gatgttgaaa acagagagg atgggtgcta    5940 tgccccaaat cagcctcaca attaagctaa gcagctaaga gtcttgcagg gtagtgtagg    6000
gaccacaggg ttaaggggggc agtagaatta tactcccact ttagtttcat ttcaaacaat    6060
ccatacacac acagccctga gcacttacaa attatactac gctctatact ttttgtttaa    6120
atgtataaat aagtggatga aagaatagat agatagacag atagatgata gatagaataa    6180
atgcttgcct tcatagctgt ctccctacct tgttcaaaat gttcctgtcc agaccaaagt    6240
accttgcctt cacttaagta atcaattcct aggttatatt ctgatgtcaa aggaagtcaa    6300
aagatgtgaa aaacaatttc tgacccacaa ctcatgcttt gtagatgact agatcaaaaa    6360
atttcagcca tatcttaaca gtgagtgaac aggaaatctc ctctttttccc tacatctgag    6420 atcccagctt ctaagacctt caattctcac tcttgatgca acagaccttg gaagtataca    6480
ggagagctga acttggtcaa caaaggagaa agtttgttg gcctccaaag gcacagctca    6540
aacttttcaa gccttctcta atcttaaagg taaacaaggg tctcatttct ttgagaactt    6600
cagggaaaat agacaaggac ttgcctggtg cttttggtag gggagcttgc actttccccc    6660
tttctggagg aaatatttat ccccaggtag ttccctttttt gcaccagtgg ttctttgaag   6720
```

```
agacttccac ctgggaacag ttaaacagca actacagggc cttgaactgc acactttcag    6780
tccggtcctc acagttgaaa agacctaagc ttgtgcctga tttaagcctt tttggtcata    6840
aaacattgaa ttctaatctc cctctcaacc ctacagtcac ccatttggta tattaaagat    6900
gtgttgtcta ctgtctagta tccctcaagc agtgtcagga attagtcatt taaatagtct    6960
gcaagccagg agtggtggct catgtctgta attccagcac ttgagaggta gaagtgggag    7020
gactgcttga gctcaagagt ttgatattat cctggacaac atagcaagac ctcgtctcta    7080
cttaaaaaaa aaaattagc caggcatgtg atgtacacct gtagtcccag ctactcagga    7140
ggtagatcct ctagagtcga cctgcaggca tgcaagctgg cactggccgt cgttttacaa    7200
cgtcgtgact gggaaaaccc tggcgttacc caacttaatc gccttgcagc acatccccct    7260
ttcgccagct ggcgtaatag cgaagaggcc cgcaccgatc gcccttccca acagttgcgc    7320
agcctgaatg gcgaatggcg cctgatgcgg tattttctcc ttacgcatct gtgcggtatt    7380
tcacaccgca tatggtgcac tctcagtaca atctgctctg atgccgcata gttaagccag    7440
ccccgacacc cgccaacacc cgctgacgcg ccctgacggg cttgtctgct cccggcatcc    7500
gcttacagac aagctgtgac cgtctccggg agctgcatgt gtcagaggtt ttcaccgtca    7560
tcaccgaaac gcgcgagacg aaagggcctc gtgatacgcc tatttttata ggttaatgtc    7620
atgataataa tggtttctta gacgtcaggt ggcacttttc ggggaaatgt gcgcggaacc    7680
cctatttgtt tatttttcta atacattca aatatgtatc cgctcatgag acaataaccc    7740
tgataaatgc ttcaataata ttgaaaaagg aagagtatga gtattcaaca tttccgtgtc    7800
gcccttattc ccttttttgc ggcattttgc cttcctgttt ttgctcaccc agaaacgctg    7860
gtgaaagtaa aagatgctga agatcagttg ggtgcacgag tgggttacat cgaactggat    7920
ctcaacagcg gtaagatcct tgagagtttt cgccccgaag aacgttttcc aatgatgagc    7980
acttttaaag ttctgctatg tggcgcggta ttatcccgta ttgacgccgg gcaagagcaa    8040
ctcggtcgcc gcatacacta ttctcagaat gacttggttg agtactcacc agtcacagaa    8100
aagcatctta cggatggcat gacagtaaga gaattatgca gtgctgccat aaccatgagt    8160
gataacactg cggccaactt acttctgaca acgatcggag gaccgaagga gctaaccgct    8220
tttttgcaca acatggggga tcatgtaact cgccttgatc gttgggaacc ggagctgaat    8280
gaagccatac caaacgacga gcgtgacacc acgatgcctg tagcaatggc aacaacgttg    8340
cgcaaactat taactggcga actacttact ctagcttccc ggcaacaatt aatagactgg    8400
atggaggcgg ataaagttgc aggaccactt ctgcgctcgg cccttccggc tggctggttt    8460
attgctgata aatctggagc cggtgagcgt gggtctcgcg gtatcattgc agcactgggg    8520
ccagatggta agccctcccg tatcgtagtt atctacacga cggggagtca ggcaactatg    8580
gatgaacgaa atagacagat cgctgagata ggtgcctcac tgattaagca ttggtaactg    8640
tcagaccaag tttactcata tatactttag attgatttaa aacttcattt ttaatttaaa    8700
aggatctagg tgaagatcct tttttgataat ctcatgacca aaatccctta acgtgagttt    8760
tcgttccact gagcgtcaga ccccgtagaa aagatcaaag gatcttcttg agatcctttt    8820
tttctgcgcg taatctgctg cttgcaaaca aaaaaaccac cgctaccagc ggtggtttgt    8880
ttgccggatc aagagctacc aactctttt ccgaaggtaa ctggcttcag cagagcgcag    8940
ataccaaata ctgttcttct agtgtagccg tagttaggcc accacttcaa gaactctgta    9000
gcaccgccta catacctcgc tctgctaatc ctgttaccag tggctgctgc cagtggcgat    9060
aagtcgtgtc ttaccgggtt ggactcaaga cgatagttac cggataaggc gcagcggtcg    9120
```

| | |
|---|---|
| ggctgaacgg ggggttcgtg cacacagccc agcttggagc gaacgaccta caccgaactg | 9180 |
| agatacctac agcgtgagct atgagaaagc gccacgcttc ccgaagggag aaaggcggac | 9240 |
| aggtatccgg taagcggcag ggtcggaaca ggagagcgca cgagggagct tccaggggga | 9300 |
| aacgcctggt atctttatag tcctgtcggg tttcgccacc tctgacttga gcgtcgattt | 9360 |
| ttgtgatgct cgtcaggggg gcggagccta tggaaaaacg ccagcaacgc ggccttttta | 9420 |
| cggttcctgg ccttttgctg ccttttgct cacatgttct ttcctgcgtt atccctgat | 9480 |
| tctgtggata accgtattac cgcctttgag tgagctgata ccgctcgccg cagccgaacg | 9540 |
| accgagcgca gcgagtcagt gagcgaggaa gcggaagagc gcccaatacg caaaccgcct | 9600 |
| ctccccgcgc gttggccgat tcattaatgc agctggcacg acaggtttcc cgactggaaa | 9660 |
| gcgggcagtg agcgcaacgc aattaatgtg agttagctca ctcattaggc accccaggct | 9720 |
| ttacacttta tgcttccggc tcgtatgttg tgtggaattg tgagcggata caatttcac | 9780 |
| acaggaaaca gctatgacat gattacgaat tcg | 9813 |

<210> SEQ ID NO 2
<211> LENGTH: 12806
<212> TYPE: DNA
<213> ORGANISM: Artificial Sequence
<220> FEATURE:
<223> OTHER INFORMATION: Polynucleotide sequence of pSVMM-beta-gal
      expression vector

<400> SEQUENCE: 2

| | |
|---|---|
| gcgcagcacc atggcctgaa ataacctctg aaagaggaac ttggttaggt accttctgag | 60 |
| gcggaaagaa ccagctgtgg aatgtgtgtc agttagggtg tggaaagtcc ccaggctccc | 120 |
| cagcaggcag aagtatgcaa agcatgcatc tcaattagtc agcaaccagg tgtggaaagt | 180 |
| ccccaggctc cccagcaggc agaagtatgc aaagcatgca tctcaattag tcagcaacca | 240 |
| tagtcccgcc cctaactccg cccatcccgc cctaactccg cccagttccg cccattctc | 300 |
| cgccccatgg ctgactaatt ttttttattt atgcagaggc cgaggccgcc tcggcctctg | 360 |
| agctattcca gaagtagtga ggaggctttt tggaggcct aggcttttgc aaaaagcttg | 420 |
| ggatctctat aatctcgcgc aacctatttt cccctcgaac acttttaag ccgtagataa | 480 |
| acaggctggg acacttcaca tgagcgaaaa atacatcgtc acctgggaca tgttgcagat | 540 |
| ccatgcacgt aaactcgcaa gccgactgat gccttctgaa caatggaaag gcattattgc | 600 |
| cgtaagccgt ggcggtctgg taccggtggg tgaagaccag aaacagcacc tcgaactgag | 660 |
| ccgcgatatt gcccagcgtt tcaacgcgct gtatggcgag atcgatcccg tcgttttaca | 720 |
| acgtcgtgac tgggaaaacc ctggcgttac ccaacttaat cgccttgcag cacatccccc | 780 |
| tttcgccagc tggcgtaata gcgaagaggc ccgcaccgat cgcccttccc aacagttgcg | 840 |
| cagcctgaat ggcgaatggc gctttgcctg gtttccggca ccagaagcgg tgccggaaag | 900 |
| ctggctggag tgcgatcttc ctgaggccga tactgtcgtc gtcccctcaa actggcagat | 960 |
| gcacggttac gatgcgccca tctacaccaa cgtgacctat cccattacgg tcaatccgcc | 1020 |
| gtttgttccc acgagaatc cgacgggttg ttactcgctc acatttaatg ttgatgaaag | 1080 |
| ctggctacag gaaggccaga cgcgaattat ttttgatggc gttaactcgg cgtttcatct | 1140 |
| gtggtgcaac gggcgctggg tcggttacgg ccaggacagt cgtttgccgt ctgaatttga | 1200 |
| cctgagcgca tttttacgcg ccggagaaaa ccgcctcgcg gtgatggtgc tgcgctggag | 1260 |
| tgacggcagt tatctggaag atcaggatat gtggcggatg agcggcattt tccgtgacgt | 1320 |

```
ctcgttgctg cataaaccga ctacacaaat cagcgatttc catgttgcca ctcgctttaa   1380
tgatgatttc agccgcgctg tactggaggc tgaagttcag atgtgcggcg agttgcgtga   1440
ctacctacgg gtaacagttt ctttatggca gggtgaaacg caggtcgcca gcggcaccgc   1500
gcctttcggc ggtgaaatta tcgatgagcg tggtggttat gccgatcgcg tcacactacg   1560
tctgaacgtc gaaaacccga aactgtggag cgccgaaatc ccgaatctct atcgtgcggt   1620
ggttgaactg cacaccgccg acggcacgct gattgaagca gaagcctgcg atgtcggttt   1680
ccgcgaggtg cggattgaaa atggtctgct gctgctgaac ggcaagccgt tgctgattcg   1740
aggcgttaac cgtcacgagc atcatcctct gcatggtcag gtcatggatg agcagacgat   1800
ggtgcaggat atcctgctga tgaagcagaa caactttaac gccgtgcgct gttcgcatta   1860
tccgaaccat ccgctgtggt acgctgtgtg cgaccgctac ggcctgtatg tggtggatga   1920
agccaatatt gaaacccacg gcatggtgcc aatgaatcgt ctgaccgatg atccgcgctg   1980
gctaccggcg atgagcgaac gcgtaacgcg aatggtgcag cgcgatcgta atcacccgag   2040
tgtgatcatc tggtcgctgg ggaatgaatc aggccacggc gctaatcacg acgcgctgta   2100
tcgctggatc aaatctgtcg atccttcccg cccggtgcag tatgaaggcg gcggagccga   2160
caccacggcc accgatatta tttgcccgat gtacgcgcgc gtggatgaag accagccctt   2220
cccggctgtg ccgaaatggt ccatcaaaaa atggctttcg ctacctggag agacgcgccc   2280
gctgatcctt tgcgaatacg cccacgcgat gggtaacagt cttggcggtt cgctaaata   2340 ctggcaggcg tttcgtcagt atccccgttt acagggcggc ttcgtctggg actgggtgga   2400
tcagtcgctg attaaatatg atgaaaacgg caacccgtgg tcggcttacg gcggtgattt   2460
tggcgatacg ccgaacgatc gccagttctg tatgaacggt ctggtctttg ccgaccgcac   2520
gccgcatcca gcgctgacgg aagcaaaaca ccagcagcag ttttttccagt tccgtttatc   2580 cgggcaaaacc atcgaagtga ccagcgaata cctgttccgt catagcgata acgagctcct   2640
gcactggatg gtggcgctgg atggtaagcc gctggcaagc ggtgaagtgc ctctggatgt   2700
cgctccacaa ggtaaacagt tgattgaact gcctgaacta ccgcagccgg agagcgccgg   2760
gcaactctgg ctcacagtac gcgtagtgca accgaacgcg accgcatggt cagaagccgg   2820
gcacatcagc gcctggcagc agtggcgtct ggcggaaaac ctcagtgtga cgctccccgc   2880
cgcgtcccac gccatcccgc atctgaccac cagcgaaatg gattttgca tcgagctggg   2940 taataagcgt tggcaattta accgccagtc aggctttctt tcacagatgt ggattggcga   3000
taaaaaacaa ctgctgacgc cgctgcgcga tcagttcacc cgtgcaccgc tggataacga   3060
cattggcgta agtgaagcga cccgcattga ccctaacgcc tgggtcgaac gctggaaggc   3120
ggcgggccat taccaggccg aagcagcgtt gttgcagtgc acggcagata cacttgctga   3180
tgcggtgctg attacgaccg ctcacgcgtg gcagcatcag gggaaaacct tatttatcag   3240
ccggaaaacc taccggattg atggtagtgg tcaaatggcg attaccgttg atgttgaagt   3300
ggcgagcgat acaccgcatc cggcgcggat tggcctgaac tgccagctgg cgcaggtagc   3360
agagcgggta aactggctcg gattagggcc gcaagaaaac tatcccgacc gccttactgc   3420
cgcctgtttt gaccgctggg atctgccatt gtcagacatg tatacccgt acgtcttccc   3480 gagcgaaaac ggtctgcgct gcgggacgcg cgaattgaat tatggcccac accagtggcg   3540
cggcgacttc cagttcaaca tcagccgcta cagtcaacag caactgatgg aaaccagcca   3600
tcgccatctg ctgcacgcgg aagaaggcac atggctgaat atcgacggtt ccatatgggg   3660
```

```
gattggtggc gacgactcct ggagcccgtc agtatcggcg gaattccagc tgagcgccgg    3720
tcgctaccat taccagttgg tctggtgtca aaataataa taaccgggca ggccatgtct     3780
gcccgtattt cgcgtaagga aatccattat gtactattta aaaacacaa acttttggat     3840 gttcggttta ttcttttct tttacttttt tatcatggga gcctacttcc cgttttttccc   3900 gatttggcta catgacatca accatatcag caaaagtgat acgggtatta ttttgccgc     3960 tatttctctg ttctcgctat tattccaacc gctgtttggt ctgctttctg acaaactcgg    4020
aacttgttta ttgcagctta taatggttac aaataaagca atagcatcac aaatttcaca    4080
aataaagcat ttttttcact gcattctagt tgtggtttgt ccaaactcat caatgtatct    4140
tatcatgtct ggatccgatt tcttcctct ttaggttctc ctttatggaa tcttctgtac     4200
tgatggccat gtccttttaac tactatgtag atatctgcta ctacctgtat tatgcctcta   4260
cctttattag cagagttatc tgtactgttg gcatgacaat catttgttaa tatgacttgc    4320
cttttccttt tctgctattc ttgatcaaat ggctcctctt tcttgctcct ctcatttctc    4380
ctgccttcac ttggacgtgc ttcacgtagt ctgtgcttat gactggatta aaaattgata    4440
tggacttatc ctaatgttgt tcgtcataat atgggtttta tggtccatta ttatttccta    4500
tgcattgatc tggagaaggc ttcaatcctt ttactctttg tggaaaatat ctgtaaacct    4560
tctggttcac tctgctatag caatttcagt ttaggctagt aagcatgagg atgcctcctt    4620
ctctgatttt tcccacagtc tgttggtcac agaataacct gagtgattac tgatgaaaga    4680
gtgagaatgt tattgatagt cacaatgaca aaaacaaac aactacagtc aaaatgtttc     4740 tcttttatt agtggttata tttcctgacc tatatctggc aggactcttt agagaggtag     4800
ctgaagctgc tgttatgacc actagaggga agaagatacc tgtggagcta atggtccaag    4860
atggtggagc cccaagcaag gaagttgtta aggagcccctt ttgattgaag gtgggtgccc    4920
ccaccttaca gggacaggac atctggatac tcctcccagt ttctccagtt tcccttttc     4980 ctaatatatc tcctgataaa atgtctatac tcacttcccc atttctaata ataaagcaaa    5040
ggctagttag taagacatca ccttgcattt tgaaaatgcc atagactttc aaaattattt    5100
catacatcgg tctttcttta tttcaagagt ccagaaatgg caacattacc tttgattcaa    5160
tgtaatggaa agagctcttt caagagacag agaaaagaat aatttaattt ctttccccac    5220
acctccttcc ctgtctctta ccctatcttc cttccttcta ccctcccat ttctctctct     5280 catttctcag aagtatattt tgaaaggatt catagcagac agctaaggct ggttttttct    5340
aagtgaagaa gtgatattga aaggtaggg ttgcatgagc cctttcagtt ttttagttta     5400
tatacatctg tattgttaga atgttttata atataaataa aattatttct cagttatata    5460
ctagctatgt aacctgtgga tatttcctta agtattacaa gctatactta actcacttgg    5520
aaaactcaaa taaatacctg cttcatagtt attaataagg attaagtgag ataatgccct    5580
ataagattcc tattaataac agataaatac atacacacac acacacattg aaaggattct    5640
tactttgtgc taggaactat aataagttca ttgatgcatt atatcattaa gttctaattt    5700
caacactaga aggcaggtat tatctaaatt tcatactgga tacctccaaa ctcataaaga    5760
taattaaatt gccttttgtc atatatttat tcaaagggt aactcaaact atggcttgtc     5820
taattttata tatcacccta ctgaacatga cccctattgtg atattttata aaattatctc   5880
aagttattat gaggatgttg aaagacagag aggatgggtg ctatgcccca aatcagcctc    5940
acaattaagc taagcagcta agagtcttgc agggtagtgt agggaccaca gggttaaggg    6000
ggcagtagaa ttatactccc actttagttt catttcaaac aatccataca cacacagccc    6060
```

```
tgagcactta caaattatac tacgctctat acttttttgtt taaatgtata aataagtgga   6120
tgaaagaata gatagataga cagatagatg atagataaga taaatgcttg ccttcatagc   6180
tgtctcccta ccttgttcaa atgttcctg tccagaccaa agtaccttgc cttcacttaa    6240
gtaatcaatt cctaggttat attctgatgt caaaggaagt caaagatgt gaaaacaat    6300 ttctgaccca caactcatgc tttgtagatg actagatcaa aaaatttcag ccatatctta   6360
acagtgagtg aacaggaaat ctcctctttt ccctacatct gagatcccag cttctaagac   6420
cttcaattct cactcttgat gcaacagacc ttggaagtat acaggagagc tgaacttggt   6480
caacaaagga gaaagtttg ttggcctcca aaggcacagc tcaaacttt caagccttct    6540 ctaatcttaa aggtaaacaa gggtctcatt tctttgagaa cttcagggaa aatagacaag   6600
gacttgcctg gtgcttttgg taggggagct tgcactttcc cccttctgg aggaaatatt    6660 tatccccagg tagttccctt tttgcaccag tggttctttg aagagacttc cacctgggaa   6720
cagttaaaca gcaactacag ggccttgaac tgcacacttt cagtccggtc ctcacagttg   6780
aaaagaccta agcttgtgcc tgatttaagc ctttttggtc ataaaacatt gaattctaat   6840
ctccctctca accctacagt cacccatttg gtatattaaa gatgtgttgt ctactgtcta   6900
gtatccctca agcagtgtca ggaattagtc atttaaatag tctgcaagcc aggagtggtg   6960
gctcatgtct gtaattccag cacttgagag gtagaagtgg gaggactgct tgagctcaag   7020
agtttgatat tatcctggac aacatagcaa gacctcgtct ctacttaaaa aaaaaaaatt   7080
agccaggcat gtgatgtaca cctgtagtcc cagctactca ggaggaatcc atatgactag   7140
tagatcctct agaactagtc atatggattc ctcctgagta gctgggacta caggtgtaca   7200
tcacatgcct ggctaatttt ttttttttaa gtagagacga ggtcttgcta tgttgtccag   7260
gataatatca aactcttgag ctcaagcagt cctcccactt ctacctctca agtgctggaa   7320
ttacagacat gagccaccac tcctggcttg cagactattt aaatgactaa ttcctgacac   7380
tgcttgaggg atactagaca gtagacaaca catctttaat ataccaaatg ggtgactgta   7440
gggttgagag ggagattaga attcaatgtt ttatgaccaa aaaggcttaa atcaggcaca   7500
agcttaggtc ttttcaactg tgaggaccgg actgaaagtg tgcagttcaa ggccctgtag   7560
ttgctgttta actgttccca ggtggaagtc tcttcaaaga accactggtg caaaaggga    7620 actacctggg gataaatatt tcctccagaa aggggaaag tgcaagctcc cctaccaaaa    7680
gcaccaggca agtccttgtc tattttccct gaagttctca agaaatgag accccttgttt   7740 acctttaaga ttagagaagg cttgaaaagt ttgagctgtg cctttggagg ccaacaaact   7800
tttctccttt gttgaccaag ttcagctctc ctgtatactt ccaaggtctg ttgcatcaag   7860
agtgagaatt gaaggtctta gaagctggga tctcagatgt agggaaaaga ggagatttcc   7920
tgttcactca ctgttaagat atggctgaaa ttttttgatc tagtcatcta caaagcatga   7980
gttgtgggtc agaaattgtt tttcacatct tttgacttcc tttgacatca gaatataacc   8040
taggaattga ttacttaagt gaaggcaagg tactttggtc tggacaggaa cattttgaac   8100
aaggtaggga gacagctatg aaggcaagca tttattctat ctatcatcta tctgtctatc   8160
tatctattct ttcatccact tatttataca tttaaacaaa aagtatagag cgtagtataa   8220
tttgtaagtg ctcagggctg tgtgtgtatg gattgtttga aatgaaacta aagtgggagt   8280
ataattctac tgcccccctta accctgtggt ccctacacta ccctgcaaga ctcttagctg   8340
cttagcttaa ttgtgaggct gatttggggc atagcaccca tcctctctgt ctttcaacat   8400
```

```
cctcataata acttgagata attttataaa atatcacaat agggtcatgt tcagtagggt    8460
gatatataaa attagacaag ccatagtttg agttacccct ttgaataaat atatgacaaa    8520
aggcaattta attatcttta tgagtttgga ggtatccagt atgaaattta gataatacct    8580
gccttctagt gttgaaatta gaacttaatg atataatgca tcaatgaact tattatagtt    8640
cctagcacaa agtaagaatc ctttcaatgt gtgtgtgtgt gtatgtattt atctgttatt    8700
aataggaatc ttatagggca ttatctcact taatccttat taataactat gaagcaggta    8760
tttatttgag ttttccaagt gagttaagta tagcttgtaa tacttaagga aatatccaca    8820
ggttacatag ctagtatata actgagaaat aattttattt atattataaa acattctaac    8880
aatacagatg tatataaact aaaaaactga aagggctcat gcaaccctac cttctcaata    8940
tcacttcttc acttagaaaa aaccagcctt agctgtctgc tatgaatcct ttcaaaatat    9000
acttctgaga aatgagagag agaaatgggg agggtagaag gaaggaagat agggtaagag    9060
acagggaagg aggtgtgggg aaagaaatta aattattctt ttctctgtct cttgaaagag    9120
ctcttttccat tacattgaat caaaggtaat gttgccattt ctggactctt gaaataaaga    9180
aagaccgatg tatgaaataa ttttgaaagt ctatggcatt tcaaaatgc aaggtgatgt    9240
cttactaact agcctttgct ttattattag aaatggggaa gtgagtatag acattttatc    9300
aggagatata ttaggaaaaa gggaaactgg agaaactggg aggagtatcc agatgtcctg    9360
tccctgtaag gtggggcac ccaccttcaa tcaaagggc tccttaacaa cttccttgct    9420
tggggctcca ccatcttgga ccattagctc cacaggtatc ttcttccctc tagtggtcat    9480
aacagcagct tcagctacct ctctaaagag tcctgccaga tataggtcag gaaatataac    9540
cactaataaa aagagaaaca ttttgactgt agttgtttgt tttttgtcat tgtgactatc    9600
aataacattc tcactctttc atcagtaatc actcaggtta ttctgtgacc aacagactgt    9660
gggaaaaatc agagaaggag gcatcctcat gcttactagc ctaaactgaa attgctatag    9720
cagagtgaac cagaaggttt acagatattt tccacaaaga gtaaaggat tgaagccttc    9780
tccagatcaa tgcataggaa ataataatgg accataaaac ccatattatg acgaacaaca    9840
ttaggataag tccatatcaa ttttttaatcc agtcataagc acagactacg tgaagcacgt    9900
ccaagtgaag gcaggagaaa tgagaggagc aagaaagagg agccatttga tcaagaatag    9960
cagaaaaagg aaaggcaagt catattaaca aatgattgtc atgccaacag tacagataac   10020
tctgctaata aaggtagagg cataatacag gtagtagcag atatctacat agtagttaaa   10080
ggacatggcc atcagtacag aagattccat aaaggagaac ctaaagagga agaaaatcgg   10140
atgtcgactc gcgactgcag gcatgcaagc tggcactggc cgtcgtttta caacgtcgtg   10200
actgggaaaa ccctggcgtt acccaactta atcgccttgc agcacatccc ctttcgcca    10260
gctggcgtaa tagcgaagag gcccgcaccg atcgcccttc ccaacagttg cgcagcctga   10320
atggcgaatg gcgcctgatg cggtattttc tccttacgca tctgtgcggt atttcacacc   10380
gcatatggtg cactctcagt acaatctgct ctgatgccgc atagttaagc cagccccgac   10440
acccgccaac acccgctgac gcgccctgac gggcttgtct gctcccggca tccgcttaca   10500
gacaagctgt gaccgtctcc gggagctgca tgtgtcagag gttttcaccg tcatcaccga   10560
aacgcgcgag acgaaagggc ctcgtgatac gcctattttt ataggttaat gtcatgataa   10620
taatggtttc ttagacgtca ggtggcactt ttcggggaaa tgtgcgcgga acccctattt   10680
gtttattttt ctaaatacat tcaaatatgt atccgctcat gagacaataa ccctgataaa   10740
tgcttcaata atattgaaaa aggaagagta tgagtattca acatttccgt gtcgccctta   10800
```

```
ttcccttttt tgcggcattt tgccttcctg tttttgctca cccagaaacg ctggtgaaag   10860
taaaagatgc tgaagatcag ttgggtgcac gagtgggtta catcgaactg gatctcaaca   10920
gcggtaagat ccttgagagt tttcgccccg aagaacgttt tccaatgatg agcactttta   10980
aagttctgct atgtggcgcg gtattatccc gtattgacgc cgggcaagag caactcggtc   11040
gccgcataca ctattctcag aatgacttgg ttgagtactc accagtcaca gaaaagcatc   11100
ttacggatgg catgacagta agagaattat gcagtgctgc cataaccatg agtgataaca   11160
ctgcggccaa cttacttctg acaacgatcg gaggaccgaa ggagctaacc gcttttttgc   11220
acaacatggg ggatcatgta actcgccttg atcgttggga accggagctg aatgaagcca   11280
taccaaacga cgagcgtgac accacgatgc ctgtagcaat ggcaacaacg ttgcgcaaac   11340
tattaactgg cgaactactt actctagctt cccggcaaca attaatagac tggatggagg   11400
cggataaagt tgcaggacca cttctgcgct cggcccttcc ggctggctgg tttattgctg   11460
ataaatctgg agccggtgag cgtgggtctc gcggtatcat tgcagcactg gggccagatg   11520
gtaagccctc ccgtatcgta gttatctaca cgacggggag tcaggcaact atggatgaac   11580
gaaatagaca gatcgctgag ataggtgcct cactgattaa gcattggtaa ctgtcagacc   11640
aagtttactc atatatactt tagattgatt taaaacttca ttttttaattt aaaaggatct   11700 aggtgaagat cctttttgat aatctcatga ccaaaatccc ttaacgtgag ttttcgttcc   11760
actgagcgtc agaccccgta gaaaagatca aaggatcttc ttgagatcct ttttttctgc   11820
gcgtaatctg ctgcttgcaa acaaaaaaac caccgctacc agcggtggtt tgtttgccgg   11880
atcaagagct accaactctt tttccgaagg taactggctt cagcagagcg cagataccaa   11940
atactgttct tctagtgtag ccgtagttag gccaccactt caagaactct gtagcaccgc   12000
ctacatacct cgctctgcta atcctgttac cagtggctgc tgccagtggc gataagtcgt   12060
gtcttaccgg gttggactca agacgatagt taccggataa ggcgcagcgg tcgggctgaa   12120
cggggggttc gtgcacacag cccagcttgg agcgaacgac ctacaccgaa ctgagatacc   12180
tacagcgtga gctatgagaa agcgccacgc ttcccgaagg gagaaaggcg gacaggtatc   12240
cggtaagcgg cagggtcgga acaggagagc gcacgaggga gcttccaggg ggaaacgcct   12300
ggtatcttta tagtcctgtc gggtttcgcc acctctgact tgagcgtcga ttttttgtgat   12360 gctcgtcagg ggggcggagc ctatggaaaa acgccagcaa cgcggccttt ttacggttcc   12420
tggccttttg ctggcctttt gctcacatgt tctttcctgc gttatcccct gattctgtgg   12480
ataaccgtat taccgccttt gagtgagctg ataccgctcg ccgcagccga acgaccgagc   12540
gcagcgagtc agtgagcgag gaagcggaag agcgcccaat acgcaaaccg cctctccccg   12600
cgcgttggcc gattcattaa tgcagctggc acgacaggtt cccgactgg aaagcgggca   12660 gtgagcgcaa cgcaattaat gtgagttagc tcactcatta ggcaccccag gctttacact   12720
ttatgcttcc ggctcgtatg ttgtgtggaa ttgtgagcgg ataacaattt cacacaggaa   12780
acagctatga catgattacg aattcg                                        12806
```

<210> SEQ ID NO 3
<211> LENGTH: 43
<212> TYPE: DNA
<213> ORGANISM: Artificial Sequence
<220> FEATURE:
<223> OTHER INFORMATION: primer

<400> SEQUENCE: 3

```
ctagtctaga cctcctgagt agctgggact acaggtgtac atc                    43

<210> SEQ ID NO 4
<211> LENGTH: 57
<212> TYPE: DNA
<213> ORGANISM: Artificial Sequence
<220> FEATURE:
<223> OTHER INFORMATION: primer

<400> SEQUENCE: 4
tagggcgccc tgcagttctt cctctttagg ttctccttta tggaatcttc tgtactg     57

<210> SEQ ID NO 5
<211> LENGTH: 10158
<212> TYPE: DNA
<213> ORGANISM: Artificial Sequence
<220> FEATURE:
<223> OTHER INFORMATION: Polynucleotide sequence of pSVMM gcsf gal
      expression vector

<400> SEQUENCE: 5
gcgcagcacc atggcctgaa ataacctctg aaagaggaac ttggttaggt accttctgag    60
gcggaaagaa ccagctgtgg aatgtgtgtc agttagggtg tggaaagtcc ccaggctccc   120
cagcaggcag aagtatgcaa agcatgcatc tcaattagtc agcaaccagg tgtggaaagt   180
ccccaggctc cccagcaggc agaagtatgc aaagcatgca tctcaattag tcagcaacca   240
tagtcccgcc cctaactccg cccatcccgc cctaactccg cccagttccg cccattctc    300 cgccccatgg ctgactaatt ttttttattt atgcagaggc cgaggccgcc tcggcctctg   360
agctattcca gaagtagtga ggaggctttt ttggaggcct aggcttttgc aaaaagcttg   420
ggatctctat aatctcgcgc aacctatttt cccctcgaac acttttttaag ccgtagataa   480 acaggctggg acacttcaca tgagcgaaaa atacatcgtc acctgggaca tgttgcagat   540
ccatgcacgt aaactcgcaa gccgactgat gccttctgaa caatggaaag cattattgc    600 cgtaagccgt ggcggtctgg taccggtggg tgaagaccag aaacagcacc tcgaactgag   660
ccgcgatatt gcccagcgtt tcaacgcgct gtatggcgag atcgatatcg attgcggccg   720
catggctgga cctgccaccc agagcccat gaagctgatg gccctgcagc tgctgctgtg    780
gcacagtgca ctctggacag tgcaggaagc cacccccctg ggccctgcca gctccctgcc   840
ccagagcttc ctgctcaagt gcttagagca agtgaggaag atccagggcg atggcgcagc   900
gctccaggag aagctggtga gtgagtgtgc cacctacaag ctgtgccacc ccgaggagct   960
ggtgctgctc ggacactctc tgggcatccc ctgggctccc ctgagcagct gccccagcca  1020
ggccctgcag ctggcaggct gcttgagcca actccatagc ggccttttcc tctaccaggg  1080
gctcctgcag gccctggaag ggatctcccc cgagttgggt ccccacttgg acacactgca  1140
gctggacgtc gccgactttg ccaccaccat ctggcagcag atggaagaac tgggaatggc  1200
ccctgccctg cagcccaccc agggtgccat gccggcttc gcctctgctt tccagcgccg  1260
ggcaggaggg gtcctggttg cctcccatct gcagagcttc ctggaggtgt cgtaccgcgt  1320
tctacgccac cttgcccagc cctgagctag catagatcta gtcgactcca ccaaccgctg  1380
tttggtctgc tttctgacaa actcggaact tgtttattgc agcttataat ggttacaaat  1440
aaagcaatag catcacaaat ttcacaaata aagcattttt ttcactgcat tctagttgtg  1500
gtttgtccaa actcatcaat gtatcttatc atgtctggat ccagatctta gggcgccctg  1560
cagttcttcc tctttaggtt ctcctttatg gaatcttctg tactgatggc catgtccttt  1620
```

```
aactactatg tagatatctg ctactacctg tattatgcct ctacctttat tagcagagtt    1680
atctgtactg ttggcatgac aatcatttgt taatatgact tgcctttcct ttttctgcta    1740
ttcttgatca aatggctcct ctttcttgct cctctcattt ctcctgcctt cacttggacg    1800
tgcttcacgt agtctgtgct tatgactgga ttaaaaattg atatggactt atcctaatgt    1860
tgttcgtcat aatatggggtt ttatggtcca ttattatttc ctatgcattg atctggagaa    1920
ggcttcaatc cttttactct tgtggaaaa tatctgtaaa ccttctggtt cactctgcta     1980
tagcaatttc agtttaggct agtaagcatg aggatgcctc cttctctgat ttttcccaca    2040
gtctgttggt cacagaataa cctgagtgat tactgatgaa agagtgagaa tgttattgat    2100
agtcacaatg acaaaaaaca aacaactaca gtcaaaatgt ttctcttttt attagtggtt    2160
atatttcctg acctatatct ggcaggactc tttagagagg tagctgaagc tgctgttatg    2220
accactagag ggaagaagat acctgtggag ctaatggtcc aagatggtgg agccccaagc    2280
aaggaagttg ttaaggagcc cttttgattg aaggtgggtg ccccaccctt acagggacag    2340
gacatctgga tactcctccc agtttctcca gtttccctttt tcctaatat atctcctgat     2400
aaaatgtcta tactcacttc cccatttcta ataataaagc aaaggctagt tagtaagaca    2460
tcaccttgca ttttgaaaat gccatagact ttcaaaatta tttcatacat cggtctttct    2520
ttatttcaag agtccagaaa tggcaacatt acctttgatt caatgtaatg gaaagagctc    2580
tttcaagaga cagagaaaag aataaattaa tttctttccc cacacctcct tccctgtctc    2640
ttaccctatc ttccttcctt ctaccctccc catttctctc tctcatttct cagaagtata    2700
ttttgaaagg attcatagca gacagctaag gctggttttt tctaagtgaa gaagtgatat    2760
tgagaaggta gggttgcatg agcccttcca gtttttagt ttatatacat ctgtattgtt      2820
agaatgtttt ataatataaa taaaattatt tctcagttat atactagcta tgtaacctgt    2880
ggatatttcc ttaagtatta caagctatac ttaactcact tggaaaactc aaataaatac    2940
ctgcttcata gttattaata aggattaagt gagataatgc cctataagat tcctattaat    3000
aacagataaa tacatacaca cacacacaca ttgaaaggat tcttactttg tgctaggaac    3060
tataataagt tcattgatgc attatatcat taagttctaa tttcaacact agaaggcagg    3120
tattatctaa atttcatact ggatacctcc aaactcataa agataattaa attgccttt    3180
gtcatatatt tattcaaaag ggtaactcaa actatggctt gtctaatttt atatatcacc    3240
ctactgaaca tgaccctatt gtgatatttt ataaaattat ctcaagttat tatgaggatg    3300
ttgaaagaca gagaggatgg gtgctatgcc ccaaatcagc ctcacaatta agctaagcag    3360
ctaagagtct tgcagggtag tgtagggacc acagggttaa gggggcagta gaattatact    3420
cccactttag tttcatttca aacaatccat acacacacag ccctgagcac ttacaaatta    3480
tactacgctc tatacttttt gtttaaatgt ataaataagt ggatgaaaga atagatagat    3540
agacagatag atgatagata gaataaatgc ttgccttcat agctgtctcc ctaccttgtt    3600
caaaatgttc ctgtccagac caaagtacct tgccttcact taagtaatca attcctaggt    3660
tatattctga tgtcaaagga agtcaaaaga tgtgaaaaac aatttctgac ccacaactca    3720
tgctttgtag atgactagat caaaaaattt cagccatatc ttaacagtga gtgaacagga    3780
aatctcctct tttccctaca tctgagatcc cagcttctaa gaccttcaat tctcactctt    3840
gatgcaacag accttggaag tatacaggag agctgaactt ggtcaacaaa ggagaaaagt    3900
ttgttggcct ccaaaggcac agctcaaact tttcaagcct tctctaatct taaaggtaaa    3960
caagggtctc atttctttga gaacttcagg gaaaatagac aaggacttgc ctggtgcttt    4020
```

```
tggtagggga gcttgcactt tccccctttc tggaggaaat atttatcccc aggtagttcc    4080 cttttttgcac cagtggttct ttgaagagac ttccacctgg gaacagttaa acagcaacta   4140
cagggccttg aactgcacac tttcagtccg gtcctcacag ttgaaaagac ctaagcttgt    4200
gcctgattta agccttttg gtcataaaac attgaattct aatctccctc tcaaccctac    4260
agtcacccat ttggtatatt aaagatgtgt tgtctactgt ctagtatccc tcaagcagtg   4320
tcaggaatta gtcatttaaa tagtctgcaa gccaggagtg gtggctcatg tctgtaattc   4380
cagcacttga gaggtagaag tgggaggact gcttgagctc aagagtttga tattatcctg   4440
gacaacatag caagacctcg tctctactta aaaaaaaaaa attagccagg catgtgatgt   4500
acacctgtag tcccagctac tcaggaggta gatcctctag acctcctgag tagctgggac   4560
tacaggtgta catcacatgc ctggctaatt tttttttttt aagtagagac gaggtcttgc   4620
tatgttgtcc aggataatat caaactcttg agctcaagca gtcctcccac ttctacctct   4680
caagtgctgg aattacagac atgagccacc actcctggct tgcagactat ttaaatgact   4740
aattcctgac actgcttgag ggatactaga cagtagacaa cacatcttta atataccaaa   4800
tgggtgactg tagggttgag agggagatta gaattcaatg ttttatgacc aaaaaggctt   4860
aaatcaggca caagcttagg tcttttcaac tgtgaggacc ggactgaaag tgtgcagttc   4920
aaggccctgt agttgctgtt taactgttcc caggtggaag tctcttcaaa gaaccactgg   4980
tgcaaaaagg gaactacctg gggataaata tttcctccag aaaggggaa agtgcaagct    5040 cccctaccaa aagcaccagg caagtccttg tctattttcc ctgaagttct caaagaaatg   5100
agacccttgt ttacctttaa gattagagaa ggcttgaaaa gtttgagctg tgcctttgga   5160
ggccaacaaa ctttctcct ttgttgacca agttcagctc tcctgtatac ttccaaggtc    5220
tgttgcatca agagtgagaa ttgaaggtct tagaagctgg gatctcagat gtagggaaaa   5280
gaggagattt cctgttcact cactgttaag atatggctga aatttttga tctagtcatc    5340 tacaaagcat gagttgtggg tcagaaattg ttttcacat cttttgactt cctttgacat    5400
cagaatataa cctaggaatt gattacttaa gtgaaggcaa ggtactttgg tctggacagg   5460 aacatttga caaggtagg gagacagcta tgaaggcaag catttattct atctatcatc     5520
tatctgtcta tctatctatt ctttcatcca cttatttata catttaaaca aaaagtatag   5580
agcgtagtat aatttgtaag tgctcagggc tgtgtgtgta tggattgttt gaaatgaaac   5640
taaagtggga gtataattct actgccccct taaccctgtg gtccctacac taccctgcaa   5700
gactcttagc tgcttagctt aattgtgagg ctgatttggg gcatagcacc catcctctct   5760
gtctttcaac atcctcataa taacttgaga taattttata aaatatcaca ataggtcat    5820 gttcagtagg gtgatatata aaattagaca agccatagtt tgagttaccc ttttgaataa   5880
atatatgaca aaaggcaatt taattatctt tatgagtttg gaggtatcca gtatgaaatt   5940 tagataaatac ctgccttcta gtgttgaaat tagaacttaa tgtataatg catcaatgaa    6000 cttattatag ttcctagcac aaagtaagaa tcctttcaat gtgtgtgtgt gtgtatgtat   6060
ttatctgtta ttaataggaa tcttataggg cattatctca cttaatcctt attaataact   6120
atgaagcagg tatttatttg agttttccaa gtgagttaag tatagcttgt aatacttaag   6180
gaaatatcca caggttacat agctagtata taactgagaa ataatttat ttatattata    6240 aaacattcta acaatacaga tgtatataaa ctaaaaaact gaaagggctc atgcaaccct   6300
accttctcaa tatcacttct tcacttagaa aaaaccagcc ttagctgtct gctatgaatc   6360
```

```
ctttcaaaat atacttctga gaaatgagag agagaaatgg ggagggtaga aggaaggaag      6420
ataggg taag agacagggaa ggaggtgtgg ggaaagaaat taaattattc ttttctctgt      6480
ctcttgaaag agctctttcc attacattga atcaaaggta atgttgccat ttctggactc      6540
ttgaaataaa gaaagaccga tgtatgaaat aattttgaaa gtctatggca ttttcaaaat      6600
gcaaggtgat gtcttactaa ctagcctttg ctttattatt agaaatgggg aagtgagtat      6660
agacatttta tcaggagata tattaggaaa aagggaaact ggagaaactg ggaggagtat      6720
ccagatgtcc tgtccctgta aggtggggge acccaccttc aatcaaaagg gctccttaac      6780
aacttccttg cttggggctc caccatcttg gaccattagc tccacaggta tcttcttccc      6840
tctagtggtc ataacagcag cttcagctac ctctctaaag agtcctgcca gatataggtc      6900
aggaaatata accactaata aaagagaaa cattttgact gtagttgttt gttttttgtc      6960
attgtgacta tcaataacat tctcactctt tcatcagtaa tcactcaggt tattctgtga      7020
ccaacagact gtgggaaaaa tcagagaagg aggcatcctc atgcttacta gcctaaactg      7080
aaattgctat agcagagtga accagaaggt ttacagatat tttccacaaa gagtaaaagg      7140
attgaagcct tctccagatc aatgcatagg aaataataat ggaccataaa acccatatta      7200
tgacgaacaa cattaggata agtccatatc aattttttaat ccagtcataa gcacagacta      7260
cgtgaagcac gtccaagtga aggcaggaga aatgagagga gcaagaaaga ggagccattt      7320
gatcaagaat agcagaaaaa ggaaaggcaa gtcatattaa caaatgattg tcatgccaac      7380
agtacagata actctgctaa taaaggtaga ggcataatac aggtagtagc agatatctac      7440
atagtagtta aaggacatgg ccatcagtac agaagattcc ataaggaga acctaaagag      7500
gaagaactgc aggcatgcaa gctggcactg gccgtcgttt tacaacgtcg tgactgggaa      7560
aaccctggcg ttacccaact taatcgcctt gcagcacatc cccctttcgc cagctggcgt      7620
aatagcgaag aggcccgcac cgatcgccct tcccaacagt tgcgcagcct gaatggcgaa      7680
tggcgcctga tgcggtattt tctccttacg catctgtgcg gtatttcaca ccgcatatgg      7740
tgcactctca gtacaatctg ctctgatgcc gcatagttaa gccagccccg acacccgcca      7800
acacccgctg acgcgccctg acgggcttgt ctgctcccgg catccgctta cagacaagct      7860
gtgaccgtct ccgggagctg catgtgtcag aggttttcac cgtcatcacc gaaacgcgcg      7920
agacgaaagg gcctcgtgat acgcctattt ttataggtta atgtcatgat aataatggtt      7980
tcttagacgt caggtggcac ttttcgggga aatgtgcgcg gaacccctat ttgtttattt      8040
ttctaaatac attcaaatat gtatccgctc atgagacaat aaccctgata aatgcttcaa      8100
taatattgaa aaaggaagag tatgagtatt caacatttcc gtgtcgccct tattccctt      8160
tttgcggcat tttgccttcc tgttttgtgct cacccagaaa cgctggtgaa agtaaaagat      8220
gctgaagatc agttgggtgc acgagtgggt tacatcgaac tggatctcaa cagcggtaag      8280
atccttgaga gttttcgccc cgaagaacgt tttccaatga tgagcacttt taaagttctg      8340
ctatgtggcg cggtattatc ccgtattgac gccgggcaag agcaactcgg tcgccgcata      8400
cactattctc agaatgactt ggttgagtac tcaccagtca cagaaaagca tcttacggat      8460
ggcatgacag taagagaatt atgcagtgct gccataacca tgagtgataa cactgcggcc      8520
aacttacttc tgacaacgat cggaggaccg aaggagctaa ccgcttttt gcacaacatg      8580
ggggatcatg taactcgcct tgatcgttgg gaaccggagc tgaatgaagc cataccaaac      8640
gacgagcgtg acaccacgat gcctgtagca atggcaacaa cgttgcgcaa actattaact      8700
ggcgaactac ttactctagc ttcccggcaa caattaatag actggatgga ggcggataaa      8760
```

```
gttgcaggac cacttctgcg ctcggcccct ccggctggct ggtttattgc tgataaatct    8820
ggagccggtg agcgtgggtc tcgcggtatc attgcagcac tggggccaga tggtaagccc    8880
tcccgtatcg tagttatcta cacgacgggg agtcaggcaa ctatggatga acgaaataga    8940
cagatcgctg agataggtgc ctcactgatt aagcattggt aactgtcaga ccaagtttac    9000
tcatatatac tttagattga tttaaaactt cattttttaat ttaaaaggat ctaggtgaag    9060
atccttttg ataatctcat gaccaaaatc ccttaacgtg agttttcgtt ccactgagcg    9120
tcagacccg tagaaaagat caaaggatct tcttgagatc ctttttttct gcgcgtaatc    9180
tgctgcttgc aaacaaaaaa accaccgcta ccagcggtgg tttgtttgcc ggatcaagag    9240
ctaccaactc tttttccgaa ggtaactggc ttcagcagag cgcagatacc aaatactgtt    9300
cttctagtgt agccgtagtt aggccaccac ttcaagaact ctgtagcacc gcctacatac    9360
ctcgctctgc taatcctgtt accagtggct gctgccagtg cgataagtc gtgtcttacc    9420
gggttggact caagacgata gttaccggat aaggcgcagc ggtcgggctg aacggggggt    9480
tcgtgcacac agcccagctt ggagcgaacg acctacaccg aactgagata cctacagcgt    9540
gagctatgag aaagcgccac gcttcccgaa gggagaaagg cggacaggta tccggtaagc    9600
ggcagggtcg gaacaggaga gcgcacgagg gagcttccag ggggaaacgc ctggtatctt    9660
tatagtcctg tcgggtttcg ccacctctga cttgagcgtc gatttttgtg atgctcgtca    9720
ggggggcgga gcctatggaa aaacgccagc aacgcggcct ttttacggtt cctggccttt    9780
tgctggcctt tgctcacat gttctttcct gcgttatccc ctgattctgt ggataaccgt    9840
attaccgcct ttgagtgagc tgataccgct cgccgcagcc gaacgaccga gcgcagcgag    9900
tcagtgagcg aggaagcgga agagcgccca atacgcaaac cgcctctccc cgcgcgttgg    9960
ccgattcatt aatgcagctg gcacgacagg tttcccgact ggaaagcggg cagtgagcgc   10020
aacgcaatta atgtgagtta gctcactcat taggcacccc aggctttaca ctttatgctt   10080
ccggctcgta tgttgtgtgg aattgtgagc ggataacaat ttcacacagg aaacagctat   10140
gacatgatta cgaattcg                                                 10158
```

<210> SEQ ID NO 6
<211> LENGTH: 8559
<212> TYPE: DNA
<213> ORGANISM: Artificial Sequence
<220> FEATURE:
<223> OTHER INFORMATION: Polynucleotide sequence of pCMV-beta-gal vector

<400> SEQUENCE: 6

```
gaattcgagc tcgcccgaca ttgattattg actagttatt aatagtaatc aattacgggg      60
tcattagttc atagcccata tatggagttc cgcgttacat tacttacggt aaatggcccg     120
cctggctgac cgcccaacga ccccgccat tgacgtcaat aatgacgtat gttcccatag     180
taacgccaat agggactttc cattgacgtc aatgggtgga gtatttacgg taaactgccc     240
acttggcagt acatcaagtg tatcatatgc caagtacgcc ccctattgac gtcaatgacg     300
gtaaatggcc cgcctggcat tatgcccagt acatgacctt atgggacttt cctacttggc     360
aagtacatct acgtattagt catcgctatt accatggtga tgcggttttg gcagtacatc     420
aatgggcgtg gatagcggtt tgactcacgg ggatttccaa gtctccaccc cattgacgtc     480
aatgggagtt tgttttggca ccaaaatcaa cgggactttc caaaatgtcg taacaactcc     540
gccccattga cgcaaatggg cggtaggcgt gtacggtggg aggtctatat aagcagagct     600
```

```
cgtttagtga accgtcagat cgcctggaga cgccatccac gctgttttga cctccataga       660
agacaccggg accgatccag cctcccgcgg ccgataacta gcagcatttc ctccaacgag       720
gatcccgcag gtaagaagct acaccggcca gtggccgggg ccgtggagcc gggggcatcc       780
ggtgcctgag acagaggtgc tcaaggcagt ctccacctttt tgtctcccct ctgcagagag      840
ccacattctg gaacatcgat ggcaattgat aagaatgcgg ccgccagtgt gatggatatc       900
tgcagaattc gcccttctca aggaaaaaag cggccgcaaa aggaaaagaa gttaaccta        960 ggcttttgca aaagcttgg gatctctata atctcgcgca acctattttc ccctcgaaca       1020
ctttttaagc cgtagataaa caggctggga cacttcacat gagcgaaaaa tacatcgtca      1080
cctgggacat gttgcagatc catgcacgta aactcgcaag ccgactgatg ccttctgaac      1140
aatgaaaagg cattattgcc gtaagccgtg gcggtctggt accggtgggt gaagaccaga      1200
aacagcacct cgaactgagc gcgatattg cccagcgttt caacgcgctg tatggcgaga       1260
tcgatcccgt cgttttacaa cgtcgtgact gggaaaaccc tggcgttacc caacttaatc      1320
gccttgcagc acatcccct ttcgccagct ggcgtaatag cgaagaggcc cgcaccgatc       1380
gcccttccca acagttgcgc agcctgaatg gcgaatggcg ctttgcctgg tttccggcac      1440
cagaagcggt gccggaaagc tggctggagt gcgatcttcc tgaggccgat actgtcgtcg      1500 tccctcaaa ctggcagatg cacggttacg atgcgcccat ctacaccaac gtgacctatc       1560
ccattacggt caatccgccg tttgttccca cggagaatcc gacgggttgt tactcgctca      1620
catttaatgt tgatgaaagc tggctacagg aaggccagac gcgaattatt tttgatggcg      1680
ttaactcggc gtttcatctg tggtgcaacg ggcgctgggt cggttacggc caggacagtc      1740
gtttgccgtc tgaatttgac ctgagcgcat ttttacgcgc cggagaaaac cgcctcgcgg      1800
tgatggtgct gcgctggagt gacggcagtt atctggaaga tcaggatatg tggcggatga      1860
gcggcatttt ccgtgacgtc tcgttgctgc ataaaccgac tacacaaatc agcgatttcc      1920
atgttgccac tcgctttaat gatgatttca gccgcgctgt actggaggct gaagttcaga      1980
tgtgcggcga gttgcgtgac tacctacggg taacagtttc tttatggcag ggtgaaacgc      2040
aggtcgccag cggcaccgcg cctttcggcg gtgaaattat cgatgagcgt ggtggttatg      2100
ccgatcgcgt cacactacgt ctgaacgtcg aaaacccgaa actgtggagc gccgaaatcc      2160
cgaatctcta tcgtgcggtg gttgaactgc acaccgccga cggcacgctg attgaagcag      2220
aagcctgcga tgtcggtttc cgcgaggtgc ggattgaaaa tggtctgctg ctgctgaacg      2280
gcaagccgtt gctgattcga ggcgttaacc gtcacgagca tcatcctctg catggtcagg      2340
tcatggatga gcagacgatg gtgcaggata tcctgctgat gaagcagaac aactttaacg      2400
ccgtgcgctg ttcgcattat ccgaaccatc cgctgtggta cacgctgtgc gaccgctacg      2460
gcctgtatgt ggtggatgaa gccaatattg aaacccacgg catggtgcca atgaatcgtc      2520
tgaccgatga tccgcgctgg ctaccggcga tgagcgaacg cgtaacgcga atggcgcagc      2580
gcgatcgtaa tcacccgagt gtgatcatct ggtcgctggg gaatgaatca ggccacggcg      2640
ctaatcacga cgcgctgtat cgctggatca atctgtcga tccttcccgc ccggtgcagt       2700
atgaaggcgg cggagccgac accacggcca ccgatattat ttgcccgatg tacgcgcgcg      2760
tggatgaaga ccagcccttc ccggctgtgc cgaaatggtc catcaaaaaa tggctttcgc      2820
tacctggaga gacgcgcccg ctgatccttt gcgaatacgc ccacgcgatg ggtaacagtc      2880
ttggcggttt cgctaaatac tggcaggcgt ttcgtcagta tccccgttta cagggcggct      2940
tcgtctggga ctgggtggat cagtcgctga ttaaatatga tgaaaacggc aacccgtggt      3000
```

```
cggcttacgg cggtgatttt ggcgatacgc cgaacgatcg ccagttctgt atgaacggtc   3060
tggtctttgc cgaccgcacg ccgcatccag cgctgacgga agcaaaacac cagcagcagt   3120
ttttccagtt ccgtttatcc gggcaaacca tcgaagtgac cagcgaatac ctgttccgtc   3180
atagcgataa cgagctcctg cactggatgg tggcgctgga tggtaagccg ctggcaagcg   3240
gtgaagtgcc tctggatgtc gctccacaag gtaaacagtt gattgaactg cctgaactac   3300
cgcagccgga gagcgccggg caactctggc tcacagtacg cgtagtgcaa ccgaacgcga   3360
ccgcatggtc agaagccggg cacatcagcg cctggcagca gtggcgtctg gcggaaaacc   3420
tcagtgtgac gctccccgcc gcgtcccacg ccatcccgca tctgaccacc agcgaaatgg   3480 attttttgcat cgagctgggt aataagcgtt ggcaatttaa ccgccagtca ggctttcttt   3540
cacagatgtg gattggcgat aaaaaacaac tgctgacgcc gctgcgcgat cagttcaccc   3600
gtgcaccgct ggataacgac attggcgtaa gtgaagcgac ccgcattgac cctaacgcct   3660
gggtcgaacg ctggaaggcg gcgggccatt accaggccga agcagcgttg ttgcagtgca   3720
cggcagatac acttgctgat gcggtgctga ttacgaccgc tcacgcgtgg cagcatcagg   3780
ggaaaacctt atttatcagc cggaaaacct accggattga tggtagtggt caaatggcga   3840
ttaccgttga tgttgaagtg gcgagcgata caccgcatcc ggcgcggatt ggcctgaact   3900
gccagctggc gcaggtagca gagcgggtaa actggctcgg attagggccg caagaaaact   3960
atcccgaccg ccttactgcc gcctgttttg accgctggga tctgccattg tcagacatgt   4020
ataccccgta cgtcttcccg agcgaaaacg gtctgcgctg cgggacgcgc gaattgaatt   4080
atggcccaca ccagtggcgc ggcgacttcc agttcaacat cagccgctac agtcaacagc   4140
aactgatgga aaccagccat cgccatctgc tgcacgcgga agaaggcaca tggctgaata   4200
tcgacggttt ccatatgggg attggtggcg acgactcctg gagcccgtca gtatcggcgg   4260
aattccagct gagcgccggt cgctaccatt accagttggt ctggtgtcaa aaataataat   4320
aaccgggcag gccatgtctg cccgtatttc gcgtaaggaa atccattatg tactatttaa   4380
aaaacacaaa cttttggatg ttcggtttat tcttttttctt ttactttttt atcatgggag   4440
cctacttccc gttttttcccg atttggctac atgacatcaa ccatatcagc aaaagtgata   4500
cgggtattat ttttgccgct atttctctgt tctcgctatt attccaaccg ctgtttggtc   4560
tgctttctga caaactcgga acttgtttat tgcagcttat aatggttaca aataaagcaa   4620
tagcatcaca aatttcacaa ataaagcatt ttttcactg cattctagtt gtggtttgtc   4680
caaactcatc aatgtatctt atcatgtctg gatccagatc ttccttaatt aaggtggttt   4740
aaacaaagct ctagctagct tccacagctg cgccaggtcc tcgatcgagt agatgtcgtg   4800
gtgcggcggc ggcgagatca ggcccacgcc cggcaccgaa tagcgcagct ggcgatgta   4860 ttccgagacc ttgtggccgg gcagctgtgg aatgtgtgtc agttagggtg tggaaagtcc   4920
ccaggctccc cagcaggcag aagtatgcaa agcatgcatc tcaattagtc agaaccagg   4980 tgtggaaagt ccccaggctc cccagcaggc acaagtatgc aaagcatgca tctcaattag   5040
tcagcaacca tagtcccgcc cctaactccg cccatcccgc ccttactccg cccagttcc   5100 gcccattctc cgccccatgg ctgactaatt ttttttattt atgcagaggc cgaggccgcc   5160
tcggcctctg agctattcca gaagtagtga ggaggctttt ttggaggcct aggcttttgc   5220
aaaaagctta tcgcgataag aggattttat ccccgctgcc atcatggttc gaccattgaa   5280
ctgcatcgtc gccgtgtccc aaaatatggg gattggcaag aacggagacc tacccctggcc   5340
```

```
tccgctcagg aacgagttca agtacttcca aagaatgacc acaacctctt cagtggaagg   5400
taaacagaat ctggtgatta tgggtaggaa aacctggttc tccattcctg agaagaatcg   5460
acctttaaag gacagaatta atatagttct cagtagagaa ctaaaagaac caccacgagg   5520
agctcatttt cttgccaaaa gtttggatga tgccttaaga cttattgaac aaccggaatt   5580
ggcaagtaaa gtagacatgg tttggatagt cggaggcagt tctgtttacc aggaagccat   5640
gaatcaacca ggccacctca gactctttgt gacaaggatc atgcaggaat ttgaaagtga   5700 cacgttttc ccagaaattg atttggggaa atataaactt ctcccagaat acccaggcgt   5760
cctctctgag gtccaggagg aaaaaggcat caagtataag tttgaaatct acgagaagaa   5820
agactaacag gaagatgctt tcaagttctc tgctcccctc ctaaagctat gcatttttat   5880
aagaccatgg gactttgct ggctttagat ccttcgcggg acgtcctttg tttacgtccc   5940
gtcggcgctg aatcccggac gacccctctc ggggccgctt gggactctct cgtcccttc   6000 tccgtctgcc gttccagccg accacggggc gcacctctct ttacgcggtc tccccgtctg   6060
tgccttctca tctgccggtc cgtgtgcact tcgcttcacc tctggacgtt gcatggagac   6120
caccgtgaac gcccatcaga tcctgcccaa ggtcttacat aagaggactc ttggactccc   6180
agcaatgtca acgaccgacc ttgaggccta cttcaaagac tgtgtgttta aggactggga   6240
ggagctgggg gaggagatta ggttaaaggt cttgtatta ggaggctgta ggcacaaatt   6300
ggtctgcgca ccagcaccat gcaacttttt cacctctgcc taatcatctc ttgtacatgt   6360
cccactgttc aagcctccaa gctgtgcctt gggtggcttt ggggcatgga cattgaccct   6420
tataaagaat ttggagctag tgtggagtta ctctcgtttt tgccttctga cttctttcct   6480
tccgtcagag atcctctacg ccggacgcat cgtggccggc atggcggccg acgcgctggg   6540
ctacgtcttg ctggcgttcg cgacgcgagg ctggatggcc ttccccatta tgattcttct   6600
cgcttccggc ggcatcggga tgcccgcgtt gcaggccatg ctgtccaggc aggtagatga   6660
cgaccatcag ggacagcttc agcaaaaggc cagcaaaagg ccaggaaccg taaaaaggcc   6720
gcgttgctgg cgtttttcca taggctccgc ccccctgacg agcatcacaa aaatcgacgc   6780
tcaagtcaga ggtggcgaaa cccgacagga ctataaagat accaggcgtt ccccctgga   6840 agctccctcg tgcgctctcc tgttccgacc ctgccgctta ccggatacct gtccgccttt   6900
ctcccttcgg gaagcgtggc gctttctcat agctcacgct gtaggtatct cagttcggtg   6960
taggtcgttc gctccaagct gggctgtgtg cacgaacccc ccgttcagcc cgaccgctgc   7020
gccttatccg gtaactatcg tcttgagtcc aacccggtaa gacacgactt atcgccactg   7080
gcagcagcca ctggtaacag gattagcaga gcgaggtatg taggcggtgc tacagagttc   7140
ttgaagtggt ggcctaacta cggctacact agaaggacag tatttggtat ctgcgctctg   7200
ctgaagccag ttaccttcgg aaaaagagtt ggtagctctt gatccggcaa acaaaccacc   7260
gctggtagcg gtggtttttt tgtttgcaag cagcagatta cgcgcagaaa aaaaggatct   7320
caagaagatc ctttgatctt ttctacgggg tctgacgctc agtggaacga aaactcacgt   7380
taagggattt tggtcatgag attatcaaaa aggatcttca cctagatcct tttaaattaa   7440
aaatgaagtt ttaaatcaat ctaaagtata tatgagtaaa cttggtctga cagttaccaa   7500
tgcttaatca gtgaggcacc tatctcagcg atctgtctat ttcgttcatc catagttgcc   7560 tgactcccg tcgtgtagat aactacgata cgggagggct taccatctgg ccccagtgct   7620
gcaatgatac cgcgagaccc acgctcaccg gctccagatt tatcagcaat aaaccagcca   7680
gccggaaggg ccgagcgcag aagtggtcct gcaactttat ccgcctccat ccagtctatt   7740
```

```
aattgttgcc gggaagctag agtaagtagt tcgccagtta atagtttgcg caacgttgtt    7800
gccattgctg caggcatcgt ggtgtcacgc tcgtcgtttg gtatggcttc attcagctcc    7860
ggttcccaac gatcaaggcg agttacatga tcccccatgt tgtgcaaaaa agcggttagc    7920
tccttcggtc ctccgatcgt tgtcagaagt aagttggccg cagtgttatc actcatggtt    7980
atggcagcac tgcataattc tcttactgtc atgccatccg taagatgctt ttctgtgact    8040
ggtgagtact caaccaagtc attctgagaa tagtgtatgc ggcgaccgag ttgctcttgc    8100
ccggcgtcaa cacgggataa taccgcgcca catagcagaa ctttaaaagt gctcatcatt    8160
ggaaaacgtt cttcggggcg aaaactctca aggatcttac cgctgttgag atccagttcg    8220
atgtaaccca ctcgtgcacc caactgatct tcagcatctt ttactttcac cagcgtttct    8280
gggtgagcaa aaacaggaag gcaaaatgcc gcaaaaaagg gaataagggc gacacggaaa    8340
tgttgaatac tcatactctt cctttttcaa tattattgaa gcatttatca gggttattgt    8400
ctcatgagcg gatacatatt tgaatgtatt tagaaaaata acaaataggg gttccgcgc    8460
acatttcccc gaaaagtgcc acctgacgtc taagaaacca ttattatcat gacattaacc    8520
tataaaaata ggcgtatcac gaggcccttt cgtcttcaa                           8559
```

<210> SEQ ID NO 7
<211> LENGTH: 14370
<212> TYPE: DNA
<213> ORGANISM: Artificial Sequence
<220> FEATURE:
<223> OTHER INFORMATION: Polynucleotide sequence of pCMVMM-beta-gal
      expression vector

<400> SEQUENCE: 7

```
gaattcgagc tcgcccgaca ttgattattg actagttatt aatagtaatc aattacgggg      60
tcattagttc atagcccata tatggagttc cgcgttacat tacttacggt aaatggcccg     120
cctggctgac cgcccaacga cccccgccat tgacgtcaat aatgacgtat gttcccatag     180
taacgccaat agggactttc cattgacgtc aatgggtgga gtatttacgg taaactgccc     240
acttggcagt acatcaagtg tatcatatgc caagtacgcc ccctattgac gtcaatgacg     300
gtaaatggcc cgcctggcat tatgcccagt acatgacctt atgggacttt cctacttggc     360
aagtacatct acgtattagt catcgctatt accatggtga tgcggttttg gcagtacatc     420
aatgggcgtg atagcggttt tgactcacgg ggatttccaa gtctccaccc cattgacgtc     480
aatgggagtt tgttttggca ccaaaatcaa cgggactttc caaaatgtcg taacaactcc     540
gccccattga cgcaaatggg cggtaggcgt gtacggtggg aggtctatat aagcagagct     600
cgtttagtga accgtcagat cgcctggaga cgccatccac gctgttttga cctccataga     660
agacaccggg accgatccag cctcccgcgg ccgataacta gcagcatttc ctccaacgag     720
gatcccgcag gtaagaagct acaccggcca gtggccgggg ccgtggagcc ggggcatcc     780
ggtgcctgag acagaggtgc tcaaggcagt ctccacctt tgtctcccct ctgcagagag     840
ccacattctg gaacatcgat ggcaattgat aagaatgcgg ccgccagtgt gatggatatc     900
tgcagaattc gcccttctca aggaaaaaag cggccgcaaa aggaaaagaa gttcctaggc     960
ttttgcaaaa agcttgggat ctctataatc tcgcgcaacc tatttccccc tcgaacactt    1020
tttaagccgt agataaacag gctgggacac ttcacatgag cgaaaaatac atcgtcacct    1080
gggacatgtt gcagatccat gcacgtaaac tcgcaagccg actgatgcct tctgaacaat    1140
ggaaaggcat tattgccgta agccgtggcg gtctggtacc ggtgggtgaa gaccagaaac    1200
```

```
agcacctcga actgagccgc gatattgccc agcgtttcaa cgcgctgtat ggcgagatcg    1260
atcccgtcgt tttacaacgt cgtgactggg aaaaccctgg cgttacccaa cttaatcgcc    1320
ttgcagcaca tccccctttc gccagctggc gtaatagcga agaggcccgc accgatcgcc    1380
cttcccaaca gttgcgcagc ctgaatgcg  aatggcgctt tgcctggttt ccggcaccag    1440
aagcggtgcc ggaaagctgg ctggagtgcg atcttcctga ggccgatact gtcgtcgtcc    1500
cctcaaactg gcagatgcac ggttacgatg cgcccatcta caccaacgtg acctatccca    1560
ttacggtcaa tccgccgttt gttcccacgg agaatccgac gggttgttac tcgctcacat    1620
ttaatgttga tgaaagctgg ctacaggaag gccagacgcg aattatttt  gatggcgtta    1680 actcggcgtt tcatctgtgg tgcaacgggc gctgggtcgg ttacgccag  acagtcgtt     1740 tgccgtctga atttgacctg agcgcatttt tacgcgccgg agaaaaccgc ctcgcggtga    1800
tggtgctgcg ctggagtgac ggcagttatc tggaagatca ggatatgtgg cggatgagcg    1860
gcattttccg tgacgtctcg ttgctgcata aaccgactac acaaatcagc gatttccatg    1920
ttgccactcg ctttaatgat gatttcagcc gcgctgtact ggaggctgaa gttcagatgt    1980
gcggcgagtt gcgtgactac ctacgggtaa cagtttcttt atggcagggt gaaacgcagg    2040
tcgccagcgg caccgcgcct ttcggcggtg aaattatcga tgagcgtggt ggttatgccg    2100
atcgcgtcac actacgtctg aacgtcgaaa acccgaaact gtggagcgcc gaaatcccga    2160
atctctatcg tgcggtggtt gaactgcaca ccgccgacgg cacgctgatt gaagcagaag    2220
cctgcgatgt cggttttcgc gaggtgcgga ttgaaaatgg tctgctgctg ctgaacggca    2280
agccgttgct gattcgaggc gttaaccgtc acgagcatca tcctctgcat ggtcaggtca    2340
tggatgagca gacgatggtg caggatatcc tgctgatgaa gcagaacaac tttaacgccg    2400
tgcgctgttc gcattatccg aaccatccgc tgtggtacac gctgtgcgac cgctacggcc    2460
tgtatgtggt ggatgaagcc aatattgaaa cccacggcat ggtgccaatg aatcgtctga    2520
ccgatgatcc gcgctggcta ccggcgatga gcgaacgcgt aacgcgaatg gtgcagcgcg    2580
atcgtaatca cccgagtgtg atcatctggt cgctggggaa tgaatcaggc cacggcgcta    2640
atcacgacgc gctgtatcgc tggatcaaat ctgtcgatcc ttcccgcccg gtgcagtatg    2700
aaggcggcgg agccgacacc acggccaccg atattatttg cccgatgtac gcgcgcgtgg    2760
atgaagacca gcccttcccg gctgtgccga atggtccat  caaaaaatgg ctttcgctac    2820
ctggagagac gcgcccgctg atcctttgcg aatacgccca cgcgatgggt aacagtcttg    2880
gcggtttcgc taaatactgg caggcgtttc gtcagtatcc ccgtttacag gcggcttcg    2940 tctgggactg ggtggatcag tcgctgatta aatatgatga aaacggcaac ccgtggtcgg    3000
cttacggcgc tgattttggc gatacgccga acgatcgcca gttctgtatg aacggtctgg    3060
tctttgccga ccgcacgccg catccagcgc tgacggaagc aaaacaccag cagcagtttt    3120
tccagttccg tttatccggg caaaccatcg aagtgaccag cgaatacctg ttccgtcata    3180
gcgataacga gctcctgcac tggatggtgg cgctggatgg taagccgctg caagcggtg     3240 aagtgcctct ggatgtcgct ccacaaggta acagttgat  tgaactgcct gaactaccgc    3300
agccggagag cgccgggcaa ctctggctca cagtacgcgt agtgcaaccg aacgcgaccg    3360
catggtcaga agccgggcac atcagcgcct ggcagcagtg gcgtctggcg gaaaacctca    3420
gtgtgacgct ccccgccgcg tcccacgcca tcccgcatct gaccaccagc gaaatggatt    3480
tttgcatcga gctgggtaat aagcgttggc aatttaaccg ccagtcaggc tttctttcac    3540
```

```
agatgtggat tggcgataaa aaacaactgc tgacgccgct gcgcgatcag ttcacccgtg    3600
caccgctgga taacgacatt ggcgtaagtg aagcgacccg cattgaccct aacgcctggg    3660
tcgaacgctg gaaggcggcg ggccattacc aggccgaagc agcgttgttg cagtgcacgg    3720
cagatacact tgctgatgcg gtgctgatta cgaccgctca cgcgtggcag catcagggga    3780
aaaccttatt tatcagccgg aaaacctacc ggattgatgg tagtggtcaa atggcgatta    3840
ccgttgatgt tgaagtggcg agcgatacac cgcatccggc gcggattggc ctgaactgcc    3900
agctggcgca ggtagcagag cgggtaaact ggctcggatt agggccgcaa gaaaactatc    3960
ccgaccgcct tactgccgcc tgttttgacc gctgggatct gccattgtca gacatgtata    4020
ccccgtacgt cttcccgagc gaaaacggtc tgcgctgcgg gacgcgcgaa ttgaattatg    4080
gcccacacca gtggcgcggc gacttccagt tcaacatcag ccgctacagt caacagcaac    4140
tgatggaaac cagccatcgc catctgctgc acgcggaaga aggcacatgg ctgaatatcg    4200
acggtttcca tatggggatt ggtgcgacg actcctggag cccgtcagta tcggcggaat    4260
tccagctgag cgccggtcgc taccattacc agttggtctg gtgtcaaaaa taataataac    4320
cgggcaggcc atgtctgccc gtatttcgcg taaggaaatc cattatgtac tatttaaaaa    4380
acacaaactt ttggatgttc ggtttattct ttttctttta cttttttatc atgggagcct    4440
acttcccgtt tttcccgatt tggctacatg acatcaacca tatcagcaaa agtgatacgg    4500
gtattatttt tgccgctatt tctctgttct cgctattatt ccaaccgctg tttggtctgc    4560
tttctgacaa actcggaact tgtttattgc agcttataat ggttacaaat aaagcaatag    4620
catcacaaat ttcacaaata aagcattttt ttcactgcat tctagttgtg gtttgtccaa    4680
actcatcaat gtatcttatc atgtctggat ccagatcttc cttaattaag gtggtttatc    4740
tgctactacc tgtattatgc ctctaccttt attagcagag ttatctgtac tgttggcatg    4800
acaatcattt gttaatatga cttgcctttc ctttttctgc tattcttgat caaatggctc    4860
ctctttcttg ctcctctcat ttctcctgcc ttcacttgga cgtgcttcac gtagtctgtg    4920
cttatgactg gattaaaaat tgatatggac ttatcctaat gttgttcgtc ataatatggg    4980
ttttatggtc cattattatt tcctatgcat tgatctggag aaggcttcaa tccttttact    5040
ctttgtggaa aatatctgta aaccttctgg ttcactctgc tatagcaatt tcagtttagg    5100
ctagtaagca tgaggatgcc tccttctctg attttttccca cagtctgttg gtcacagaat    5160
aacctgagtg attactgatg aaagagtgag aatgttattg atagtcacaa tgacaaaaaa    5220
caaacaacta cagtcaaaat gtttctcttt ttattagtgg ttatatttcc tgacctatat    5280
ctggcaggac tctttagaga ggtagctgaa gctgctgtta tgaccactag agggaagaag    5340
atacctgtgg agctaatggt ccaagatggt ggagccccaa gcaaggaagt tgttaaggag    5400 ccctttttgat tgaaggtggg tgcccccacc ttacagggac aggacatctg gatactcctc    5460
ccagtttctc cagtttccct ttttcctaat atatctcctg ataaaatgtc tatactcact    5520
tccccatttc taataataaa gcaaaggcta gttagtaaga catcaccttg cattttgaaa    5580
atgccataga ctttcaaaat tatttcatac atcggtcttt ctttatttca agagtccaga    5640
aatggcaaca ttacctttga ttcaatgtaa tggaaagagc tctttcaaga gacagagaaa    5700
agaataattt aatttctttc cccacacctc cttccctgtc tcttaccctc tcttccttcc    5760 ttctacccte cccatttctc tctctcattt ctcagaagta tattttgaaa ggattcatag    5820
cagacagcta aggctggttt tttctaagtg aagaagtgat attgagaagg tagggttgca    5880
tgagcccttt cagttttta gtttatatac atctgtattg ttagaatgtt ttataatata    5940
```

```
aataaaatta tttctcagtt atatactagc tatgtaacct gtggatattt ccttaagtat   6000
tacaagctat acttaactca cttggaaaac tcaaataaat acctgcttca tagttattaa   6060
taaggattaa gtgagataat gccctataag attcctatta ataacagata aatacataca   6120
cacacacaca cattgaaagg attcttactt tgtgctagga actataataa gttcattgat   6180
gcattatatc attaagttct aatttcaaca ctagaaggca ggtattatct aaatttcata   6240
ctggatacct ccaaactcat aaagataatt aaattgcctt tgtcatata tttattcaaa    6300 agggtaactc aaactatggc ttgtctaatt ttatatatca ccctactgaa catgaccccta  6360 ttgtgatatt ttataaaatt atctcaagtt attatgagga tgttgaaaga cagagaggat   6420
gggtgctatg ccccaaatca gcctcacaat taagctaagc agctaagagt cttgcagggt   6480
agtgtaggga ccacagggtt aaggggcag tagaattata ctcccacttt agtttcattt     6540
caaacaatcc atacacacac agccctgagc acttacaaat tatactacgc tctatacttt   6600
ttgtttaaat gtataaataa gtggatgaaa gaatagatag atagacagat agatgataga   6660
tagaataaat gcttgccttc atagctgtct ccctaccttg ttcaaaatgt tcctgtccag   6720
accaaagtac cttgccttca cttaagtaat caattcctag gttatattct gatgtcaaag   6780
gaagtcaaaa gatgtgaaaa acaatttctg acccacaact catgctttgt agatgactag   6840
atcaaaaaat ttcagccata tcttaacagt gagtgaacag gaaatctcct cttttcccta   6900
catctgagat cccagcttct aagaccttca attctcactc ttgatgcaac agaccttgga   6960
agtatacagg agagctgaac ttggtcaaca aaggagaaaa gtttgttggc ctccaaaggc   7020
acagctcaaa cttttcaagc cttctctaat cttaaaggta aacaagggtc tcatttcttt    7080
gagaacttca gggaaaatag acaaggactt gcctggtgct tttggtaggg agcttgcac    7140 tttccccctt tctggaggaa atatttatcc ccaggtagtt cccttttgc accagtggtt    7200 ctttgaagag acttccacct gggaacagtt aaacagcaac tacagggcct tgaactgcac   7260
actttcagtc cggtcctcac agttgaaaag acctaagctt gtgcctgatt taagcctttt   7320
tggtcataaa acattgaatt ctaatctccc tctcaaccct acagtcaccc atttggtata   7380
ttaaagatgt gttgtctact gtctagtatc cctcaagcag tgtcaggaat tagtcattta   7440
aatagtctgc aagccaggag tggtggctca tgtctgtaat tccagcactt gagaggtaga   7500
agtgggagga ctgcttgagc tcaagagttt gatattatcc tggacaacat agcaagacct   7560
cgtctctact taaaaaaaaa aaattagcca ggcatgtgat gtacacctgt agtcccagct   7620
actcaggagg tctagaggat ctactagtca tatggattcc tcctgagtag ctgggactac   7680
aggtgtacat cacatgcctg gctaattttt ttttttaag tagagacgag gtcttgctat    7740
gttgtccagg ataatatcaa actcttgagc tcaagcagtc ctcccacttc tacctctcaa   7800
gtgctggaat tacagacatg agccaccact cctggcttgc agactattta aatgactaat   7860
tcctgacact gcttgaggga tactagacag tagacaacac atctttaata taccaaatgg   7920
gtgactgtag ggttgagagg gagattagaa ttcaatgttt tatgaccaaa aaggcttaaa   7980
tcaggcacaa gcttaggtct tttcaactgt gaggaccgga ctgaaagtgt gcagttcaag   8040
gccctgtagt tgctgtttaa ctgttcccag gtggaagtct cttcaagaa ccactggtgc    8100 aaaaagggaa ctacctgggg ataaatattt cctccagaaa ggggaaagt gcaagctccc    8160 ctaccaaaag caccaggcaa gtccttgtct attttccctg aagttctcaa agaaatgaga   8220
cccttgttta cctttaagat tagagaaggc ttgaaaagtt tgagctgtgc ctttggaggc   8280
```

```
caacaaactt ttctcctttg ttgaccaagt tcagctctcc tgtatacttc caaggtctgt    8340
tgcatcaaga gtgagaattg aaggtcttag aagctgggat ctcagatgta gggaaaagag    8400
gagatttcct gttcactcac tgttaagata tggctgaaat ttttttgatct agtcatctac   8460
aaagcatgag ttgtgggtca gaaattgttt ttcacatctt ttgacttcct ttgacatcag    8520
aatataacct aggaattgat tacttaagtg aaggcaaggt actttggtct ggacaggaac    8580
attttgaaca aggtagggag acagctatga aggcaagcat ttattctatc tatcatctat    8640
ctgtctatct atctattctt tcatccactt atttatacat ttaaacaaaa agtatagagc    8700
gtagtataat ttgtaagtgc tcagggctgt gtgtgtatgg attgtttgaa atgaaactaa    8760
agtgggagta taattctact gcccccttaa ccctgtggtc cctacactac cctgcaagac    8820
tcttagctgc ttagcttaat tgtgaggctg atttggggca tagcacccat cctctctgtc    8880
tttcaacatc ctcataataa cttgagataa ttttataaaa tatcacaata gggtcatgtt    8940
cagtagggtg atatataaaa ttagacaagc catagtttga gttacccttt tgaataaata    9000
tatgacaaaa ggcaatttaa ttatcttat gagtttggag gtatccagta tgaaatttag     9060
ataatacctg ccttctagtg ttgaaattag aacttaatga tataatgcat caatgaactt    9120
attatagttc ctagcacaaa gtaagaatcc tttcaatgtg tgtgtgtgtg tatgtatta     9180
tctgttatta ataggaatct tatagggcat tatctcactt aatccttatt aataactatg    9240
aagcaggtat ttatttgagt tttccaagtg agttaagtat agcttgtaat acttaaggaa    9300
atatccacag gttacatagc tagtatataa ctgagaaata attttattta tattataaaa    9360
cattctaaca atacagatgt atataaacta aaaaactgaa agggctcatg caaccctacc    9420
ttctcaatat cacttcttca cttagaaaaa accagcctta gctgtctgct atgaatcctt    9480
tcaaaatata cttctgagaa atgagagaga gaaatgggga gggtagaagg aaggaagata    9540
gggtaagaga cagggaagga ggtgtgggga aagaaattaa attattcttt tctctgtctc    9600
ttgaaagagc tctttccatt acattgaatc aaaggtaatg ttgccatttc tggactcttg    9660
aaataaagaa agaccgatgt atgaaataat tttgaaagtc tatggcattt tcaaaatgca    9720
aggtgatgtc ttactaacta gccttttgctt tattattaga aatgggaag tgagtataga     9780
cattttatca ggagatatat taggaaaaag ggaaactgga gaaactggga ggagtatcca    9840
gatgtcctgt ccctgtaagg tgggggcacc caccttcaat caaaagggct ccttaacaac    9900
ttccttgctt ggggctccac catcttggac cattagctcc acaggtatct tcttccctct    9960
agtggtcata acagcagctt cagctacctc tctaaagagt cctgccagat ataggtcagg   10020
aaatataacc actaataaaa agagaaacat tttgactgta gttgtttgtt ttttgtcatt   10080
gtgactatca ataacattct cactctttca tcagtaatca ctcaggttat tctgtgacca   10140
acagactgtg ggaaaatca gagaaggagg catcctcatg cttactagcc taaactgaaa    10200
ttgctatagc agagtgaacc agaaggttta cagatatttt ccacaaagag taaaggatt    10260
gaagccttct ccagatcaat gcataggaaa taataatgga ccataaaacc catattatga   10320
cgaacaacat taggataagt ccatatcaat ttttaatcca gtcataagca cagactacgt   10380
gaagcacgtc caagtgaagg caggagaaat gagaggagca agaaagagga gccatttgat   10440
caagaatagc agaaaaagga aaggcaagtc atattaacaa atgattgtca tgccaacagt   10500
acagataact ctgctaataa aggtagaggc ataatacagg tagtagcaga taaacaaagc   10560
tctagctagc ttccacagct gcgccaggtc ctcgatcgag tagatgtcgt ggtgcggcgg   10620
cggcgagatc aggcccacgc ccggcaccga atagcgcagc ttggcgatgt attccgagac   10680
```

```
cttgtggccg ggcagctgtg gaatgtgtgt cagttagggt gtggaaagtc cccaggctcc   10740
ccagcaggca gaagtatgca aagcatgcat ctcaattagt cagaaccag gtgtggaaag    10800 tccccaggct ccccagcagg cacaagtatg caaagcatgc atctcaatta gtcagcaacc   10860
atagtcccgc ccctaactcc gcccatcccg cccttactc cgcccagttc cgcccattct    10920
ccgccccatg gctgactaat tttttttatt tatgcagagg ccgaggccgc ctcggcctct   10980
gagctattcc agaagtagtg aggaggcttt tttggaggcc taggcttttg caaaaagctt   11040
atcgcgataa gaggatttta tccccgctgc catcatggtt cgaccattga actgcatcgt   11100
cgccgtgtcc caaaatatgg ggattggcaa gaacggagac ctaccctggc ctccgctcag   11160
gaacgagttc aagtacttcc aaagaatgac cacaacctct tcagtggaag gtaaacagaa   11220
tctggtgatt atgggtagga aaacctggtt ctccattcct gagaagaatc gacctttaaa   11280
ggacagaatt aatatagttc tcagtagaga actaaaagaa ccaccacgag gagctcattt   11340
tcttgccaaa agtttggatg atgccttaag acttattgaa caaccggaat tggcaagtaa   11400
agtagacatg gtttggatag tcggaggcag ttctgtttac caggaagcca tgaatcaacc   11460
aggccacctc agactctttg tgacaaggat catgcaggaa tttgaaagtg acacgttttt   11520
cccagaaatt gatttgggga aatataaact tctcccagaa tacccaggcg tcctctctga   11580
ggtccaggag gaaaaaggca tcaagtataa gtttgaaatc tacgaagaa aagactaaca    11640 ggaagatgct ttcaagttct ctgctcccct cctaaagcta tgcattttta taagaccatg   11700 ggactttgc tggctttaga tccttcgcgg gacgtccttt gtttacgtcc cgtcggcgct    11760
gaatcccgga cgacccctct cggggccgct tgggactctc tcgtcccctt ctccgtctgc   11820
cgttccagcc gaccacgggg cgcacctctc tttacgcggt ctccccgtct gtgccttctc   11880
atctgccggt ccgtgtgcac ttcgcttcac ctctggacgt tgcatggaga ccaccgtgaa   11940
cgcccatcag atcctgccca aggtcttaca taagaggact cttggactcc cagcaatgtc   12000
aacgaccgac cttgaggcct acttcaaaga ctgtgtgttt aaggactggg aggagctggg   12060
ggaggagatt aggttaaagg tctttgtatt aggaggctgt aggcacaaat tggtctgcgc   12120
accagcacca tgcaacttt tcacctctgc ctaatcatct cttgtacatg tcccactgtt    12180
caagcctcca agctgtgcct tgggtggctt tggggcatgg acattgaccc ttataaagaa   12240
tttggagcta gtgtggagtt actctcgttt ttgccttctg acttctttcc ttccgtcaga   12300
gatcctctac gccggacgca tcgtggccgg catggcggcc gacgcgctgg gctacgtctt   12360
gctggcgttc gcgacgcgag gctggatggc cttccccatt atgattcttc tcgcttccgg   12420
cggcatcggg atgcccgcgt tgcaggccat gctgtccagg caggtagatg acgaccatca   12480
gggacagctt cagcaaaagg ccagcaaaag gccaggaacc gtaaaaaggc cgcgttgctg   12540
gcgtttttcc ataggctccg ccccctgac gagcatcaca aaaatcgacg ctcaagtcag    12600
aggtggcgaa acccgacagg actataaaga taccaggcgt ttccccctgg aagctccctc   12660
gtgcgctctc ctgttccgac cctgccgctt accggatacc tgtccgcctt tctcccttcg   12720
ggaagcgtgg cgctttctca tagctcacgc tgtaggtatc tcagttcggt gtaggtcgtt   12780
cgctccaagc tgggctgtgt gcacgaaccc ccgttcagc ccgaccgctg cgccttatcc    12840
ggtaactatc gtcttgagtc aacccggta agacacgact tatcgccact ggcagcagcc    12900
actggtaaca ggattagcag agcgaggtat gtaggcggtg ctacagagtt cttgaagtgg   12960
tggcctaact acggctacac tagaaggaca gtatttggta tctgcgctct gctgaagcca   13020
```

```
gttaccttcg gaaaaagagt tggtagctct tgatccggca aacaaaccac cgctggtagc    13080
ggtggttttt ttgtttgcaa gcagcagatt acgcgcagaa aaaaggatc tcaagaagat     13140 cctttgatct tttctacggg gtctgacgct cagtggaacg aaaactcacg ttaagggatt    13200
ttggtcatga gattatcaaa aaggatcttc acctagatcc tttaaatta aaaatgaagt     13260 tttaaatcaa tctaaagtat atatgagtaa acttggtctg acagttacca atgcttaatc    13320
agtgaggcac ctatctcagc gatctgtcta tttcgttcat ccatagttgc ctgactcccc    13380
gtcgtgtaga taactacgat acgggagggc ttaccatctg gccccagtgc tgcaatgata    13440
ccgcgagacc cacgctcacc ggctccagat ttatcagcaa taaccagcc agccggaagg     13500 gccgagcgca gaagtggtcc tgcaacttta tccgcctcca tccagtctat taattgttgc    13560
cgggaagcta gagtaagtag ttcgccagtt aatagtttgc gcaacgttgt tgccattgct    13620
gcaggcatcg tggtgtcacg ctcgtcgttt ggtatggctt cattcagctc cggttcccaa    13680
cgatcaaggc gagttacatg atcccccatg ttgtgcaaaa aagcggttag ctccttcggt    13740
cctccgatcg ttgtcagaag taagttggcc gcagtgttat cactcatggt tatggcagca    13800
ctgcataatt ctcttactgt catgccatcc gtaagatgct tttctgtgac tggtgagtac    13860
tcaaccaagt cattctgaga atagtgtatg cggcgaccga gttgctcttg cccggcgtca    13920
acacgggata ataccgcgcc acatagcaga actttaaaag tgctcatcat tggaaaacgt    13980
tcttcggggc gaaaactctc aaggatctta ccgctgttga gatccagttc gatgtaaccc    14040
actcgtgcac ccaactgatc ttcagcatct tttactttca ccagcgtttc tgggtgagca    14100
aaaacaggaa ggcaaaatgc cgcaaaaaag ggaataaggg cgacacggaa atgttgaata    14160
ctcatactct tcctttttca atattattga agcatttatc agggttattg tctcatgagc    14220
ggatacatat ttgaatgtat ttagaaaaat aaacaaatag gggttccgcg cacatttccc    14280
cgaaaagtgc cacctgacgt ctaagaaacc attattatca tgacattaac ctataaaaat    14340
aggcgtatca cgaggccctt tcgtcttcaa                                     14370
```